United States Patent [19]

Haber

[11] 4,146,454
[45] * Mar. 27, 1979

[54] ELECTROMOLECULAR PROPULSION IN DIVERSE SEMICONDUCTIVE MEDIA

[75] Inventor: Norman Haber, Old Tappan, N.J.

[73] Assignee: Haber Instruments, Inc., Palisades Park, N.J.

[*] Notice: The portion of the term of this patent subsequent to Oct. 5, 1993, has been disclaimed.

[21] Appl. No.: 707,532

[22] Filed: Jul. 22, 1976

Related U.S. Application Data

[63] Continuation-in-part of Ser. No. 102,120, Dec. 28, 1970, Pat. No. 3,989,298.

[51] Int. Cl.$^2$ ............................................. G01N 27/26
[52] U.S. Cl. ............................ 204/180 S; 204/180 R; 204/180 G; 204/299 R; 23/230 B; 424/12
[58] Field of Search ............ 204/180 R, 180 S, 180 G, 204/299, 181; 424/12; 23/230 B

[56] References Cited

U.S. PATENT DOCUMENTS

| | | | |
|---|---|---|---|
| 3,042,597 | 7/1962 | Schumacher | 204/180 R |
| 3,255,100 | 6/1966 | Raymond | 204/180 G |
| 3,567,611 | 3/1971 | Michel et al. | 204/180 G |
| 3,964,992 | 6/1976 | Krotz | 204/180 G X |
| 4,030,995 | 6/1977 | Starkweather | 204/180 S X |

*Primary Examiner*—Arthur C. Prescott

[57] ABSTRACT

This application is directed to an electromotive process for exciting a chemical species which includes orientating, re-positioning and transporting and for the separation of chemical species on a support. Unlike conventional semiconductive technology in the solid state and amorphous state, the present process is directed to electrically induced molecular transport in semiconductive media, as distinct from charge transport alone. The semiconductive medium is generally of the liquid, gas or gel form.

The process of this invention is characterized by a high mobility rate in the separation process which is achieved by tailoring a semiconductive medium for operation over a wide range of voltages at low current density. The voltage applied is preferably in the range of about 0.05 to about 25,000 volts/cm. The semiconductive media used in this invention generally comprise several components which are chosen to give a current density in the range of about 0.001 to 400 micro amp/cm$^2$ on filter paper as a substrate. The media should also have a high boiling point. A further aspect of the process is that an external cooling means is not ordinarily required.

35 Claims, No Drawings

ELECTROMOLECULAR PROPULSION IN DIVERSE SEMICONDUCTIVE MEDIA

THE INVENTION

This application is a continuation-in-part of copending application Serial No. 102,120, filed December 28, 1970, now U.S. Pat. No. 3,984,298.

This invention pertains to a method of exciting a chemical species to achieve mobility for orientating, repositioning and transporting the species and for separation among species achieved by operation at the appropriate conductivity range of the media and especially within the semiconductive range when induced by means of intense electrical fields at or near minimum and optimum current levels. Such systems are characterized by extremely fast molecular motion, or transport, hereinafter called electromolecular propulsion (EMP), as well as by great differentiation or resolution of molecular species. Such resolution is capable of accomplishing very refined analytical separations.

By comparison with conventional techniques, heretofore unobtainable or unique mobilities as well as system versatility can be achieved. This invention provides a method for inducing mobility of molecules previously considered nonmobile due to their nonpolar nature. In the case of polar molecules, such as certain metal derivatives, a greater resolution is obtained than that achieved with conventional conductive or aqueous electrolytes. These, plus additional useful factors favoring this technique, permit exceedingly high resolution separation or purification of different types of molecular species to be efficiently and very rapidly achieved. Suitable detection and/or separation means gives this process an important utility for analytical, purification, and production procedures. It also serves as a research tool for the study, characterization and elucidation of structural and physical-chemical attributes of chemical systems, materials and their interactions.

An aspect of this invention pertains to the preparation of suitable media and systems, within which the semiconductive molecular transport can be reliably accomplished. This can be performed in various media; it being generally convenient to utilize liquids for the mobile phase. The conductivity of the entire system or process is brought within the semiconductive range by adjusting the conductivity level of the media constituting the mobile phase. Very high voltages may be sustained at low current levels such that the thermoelectric heat buildup ($I^2RT$) nevertheless permits usage of readily available materials and techniques for working systems. In contrast to conventional electrochemical transport methods, in this invention very minute current levels are actually required which correspond to the semiconductive nature of the process. This often precludes the need for employing external heat convective means and permits small working configurations and small power supply size requirements. Another advantage of the process is that at the low heat levels of this invention thermal interference is minimized. The very low current levels which suffice in this invention are near optimum for molecular movement as induced by the attractive-repulsive interaction within the electric field, and, under such conditions, a very intense migratory effect can be induced which is proportional to the voltage potential applied. This migratory effect is characteristic for the molecular nature of the material and may be sharply differentiated from even similarly or related, though unidentically structured, molecules. The characteristic mobility of a substance in cm/sec may be used to classify or identify substances. The great degree of molecular resolution or differentiation may be accomplished over the distance of a few inches in a matter of seconds or minutes wherein proportionately less time is required over small instances or by the use of higher voltages. I have discovered that certain low current levels are near optimum for the EMP process and are defined herein as threshold level function dependent upon the molecular nature of the materials involved. The threshold refers to excitation level states in a solvation-adsorption system. The usual observed ranges are $2 \times 10^{-7}$ to $1.6 \times 10^{-5}$ amp/cm$^2$ for a cellulose substrate. Such threshold levels refer to minimal current requirements for initiating the EMP process and are usually close to the optimum current requirements for a given system. The semiconductive range refers to methods to achieve suitable conductivity at high voltage at the threshold range. The media used are capable of sustaining high voltage electrical fields and are tailored to have a chemically adjusted and/or controlled level of conductivity internal to the mobile phase and in combination with the substrate, by techniques consistent with the various electrical, chemical and operative requirements of the working system.

Under such conditions an intense compulsive response with very fast mobility or orientation and high resolution separation of molecular types are readily achieved. Such systems are very convenient and advantageous to operate. Their efficiency is high; heat loss is a minimum, and they are applicable within aqueous, hydrophobic and otherwise non-aqueous media.

This process may be accomplished as a liquid-state semiconductive transport or gaseous state semiconductive transport. Due to its ability to effect molecular transpositions and its use of a mobile phase, it is a semiconductive fluidic process. This distinguishes it from the sessile solid state and amorphous semiconductive systems. By virtue of its effect upon the electromolecular nature of materials through induction by and reaction to suitably intense electrical fields this process has applications to major classes of known molecular materials including inorganic ions, organic molecules, colloids, and crystalloids. Thus, this process is applicable to inorganic materials such as derived from iron, copper, nickel, cobalt, rare earths, heavy metals, zirconium, and the separation of ionic-solvate species of metal derivatives. It is also applicable to other materials such as proteins, antibiotics, vitamins, antihistamines, amino acids, dyestuffs and blood constituents.

By virtue of the extremely great resolution which can be obtained by application of EMP and the very great speed with which such separations can be achieved, and the various types of systems in which the process can be applied, it offers advantages and applications to various fields and operative procedures, including: analytical chemistry, quality control, clinical chemistry; research; preparative chemistry; physical chemistry; purification; extraction; process control; applied chemistry; and semiconductive technology.

By way of illustration, in preparative chemistry, chemical reactions conducted under suitable EMP conditions can be used to displace reaction equilibria to favor certain yields. It offers a means for selective depletion of equilibrium product from the sphere of the reaction zone, or of contaminants, or byproducts. In extraction, EMP acts as a minimal time consuming process especially from thin-walled materials, particulates, or porous substances. In applied chemistry, it is useful where very rapid and/or selective penetrative processing is desired, e.g., in dyeing or destaining fabrics. The dyes or other detectable molecules in a mixture may be individually deposited in a preselected or ordered pattern by control of their EMP response.

Another advantage of the invention is that it permits the separation, characterization, or study of molecular types by virtue of the differential threshold levels. It permits control at different levels under various conditions of pH, temperatures, different media, or other internal or external factors. An application of this would be a process which is controllable by first operating the system at the lower threshold level to effect the first separation; then going on to subsequent levels in order to complete the resolution.

Major operative features for the practice of the invention are:

1. Adjusting the operative phase to the semiconductive range to provide operation at or near molecular threshold levels and maximum or convenient voltage levels capable of being sustained by the system.
2. Establishing the optimum current level at or near the molecular threshold level at the given voltage for effective molecular resolution.
3. Utilizing those components within the system and arranging the system characteristics such that overall stability, reproducibility, and safety, are attained.

A useful analogy of this phenomena and its relationship to electrochemistry is the comparison of solid state semiconductive physics with its earlier thermionic electrical technology. Some similarities may be noted from the following characteristics of the EMP process.

1. Power supply wattage (and size) requirements are minimized.
2. Minimal electrothermal losses permit small working dimensions and increased field intensities; this contributes to fast resolution times at low distortion levels.
3. The deteriorating influence upon the system as a result of brute force power requirements, and its attendant heat effects, is eliminated. For example, at higher current densities than those used in this invention the mobility and resolution character of molecuar species may be altered.
4. The degree and manner of the electrical utilization is not restricted to the more conventional conductivity modes, such as aqueous electrolyte ion transport in liquid phase. Therefore, vast numbers of different types of materials may be acted upon, studied, or utilized in the EMP process. This includes materials and systems whose electrical or ionic contribution would be thought meager from anticipation of their molecular structures. Additionally, a broad range of nonaqueous, hydrophobic, and otherwise nonpolar substances as well as ionic, polar, covalent, aprotic, or other types of conductive substances may be included. This semiconductive fluidic process thereby serves as a new and convenient tool to explore various aspects within these fields, some of which are relatively unknown; as well as to elucidate molecular structure, excitation states, electromolecular interaction and nature of materials.
5. Operation at or near the low threshold levels can be achieved with an overall high electrical propulsive efficiency. These thresholds are characteristic for a material and generally exist at very low power levels. This then defines an operational propulsive efficiency whereby this process is capable of use at power levels just sufficient to effect the molecular species' propulsion, and wherein the electrothermal losses approach negligible values. Actually, thermal increments become negligible at very low power levels, especially in a low efficiency electrothermal system. Counteracting factors include evaporative cooling, reservoir heat capacity, thermal convection, and in certain situations dissipation by convective factors such as electroendosmotic streaming. By the controlled operation at increasing threshold levels the molecular species in turn will be inducted into propulsion at their appropriate and characteristic level irrespective of other materials which may be present. This provides an additional high resolution technique which is capable of differential molecular discrimination. This discriminatory process is further enhanced by virtue of the propulsion rate also being characteristic for the molecular species involved. This migratory or propulsive rate can be caused to vary substantially by modification of the media.

Appropriate to the mechanism of propulsion threshold it is noted that this behavior determines that point where the molecular attraction or adhesion to the substrate (surface) is counteracted by the total energy input. This is comprised of the external electrical energy input plus what other distribution is due to additional partition functions present. The molecules are then free to migrate or be swept by electrical attraction or other convective factors. The electrical characteristics of the systems show a nonlinearity as the current will gradually rise after the initial application of a given voltage. The preferred systems rapidly stabilize and remain in electrical equilibrium during the separatory process, although the process may be carried out as gradual changes occur in the electrical characteristics. In cases where a lack of stability causes difficulty but the medium is otherwise considered useful, the rate of change in resistance of the system may be reduced by the addition of an external resistance of sufficient magnitude, for example, about equal to or greater than the magnitude of the internal resistance of the system. Alternatively, an active electrical element may be utilized which is capable of sensing the current-voltage or temperature levels within a system and serve to regulate these factors or changes therein by means of control of the power source. This procedure is also of value as a safety feature.

Investigation of components for media formulation has shown that certain compound combinations are not feasible for use in EMP if stable current levels are desired. When a constant voltage is applied, these combinations continually exhibit a different resistance as if a capacitor were being charged. This effect may be illustrated by considering the variation of current with time at constant voltage, for a time on the order of several seconds or minutes.

A material or mixture with electrical characteristics of a first type A (continually increasing current) may eventually suffer arcing over. A material or mixture of a second type C (increasing current, and then decreasing current after a point) is subject to evaporative heating and so eventually burns, chars or dries out. A material or mixture of type a third B initially increasing current to a relatively constant value is a preferable media from the point of view of electrical control because it allows reproducibility of runs and readjustment of the electrical characteristics is not a concern. Materials exhibiting electrical behavior of type A may be deliberately chosen as media components to offset the properties of a media which otherwise exhibits type C behavior, and vice versa. Also, the electrical characteristics of a given compound may change depending on the other substances with which it is mixed. Examples of compounds illustrating type A behavior in some mixtures and type B behavior in others is given below. Generally one would choose a media component which exhibits type B behavior in conjunction with the other components in the system.

| COMPOUNDS | TYPE BEHAVIOR |
|---|---|
| N,N-dimethylacetamide in water | A |
| N,N-dimethylacetamide in formamide | A |
| N,N-dimethylformamide in water | B |
| 1,2-propanediolcyclic carbonate in water | A |
| ethylene carbonate in water | B |
| 3-methyl sulfolane in water | A |
| 2-pyrrolidinone in water | A |
| N-methylformamide in water | A |
| N-methylacetamide in water | B |
| tetrahydrofurfuryl alcohol in water | B |
| tetrahydrothiophene dioxide in formamide | A |
| diacetone alcohol in formamide | A |
| diacetone alcohol in thiodiethylene glycol | B |
| cellosolve in formamide | A |
| cellosolve in thiodiethylene glycol | B |

The EMP process differs from the prior art processes of electrophoresis and dielectrophoresis in a number of respects. EMP exhibits non-linear electrical characteristics departing from the Kohlrausch requirement for electrolytes and from Ohm's Law. Specifically, the following characteristics are observed with EMP (1) non-doubling of current with doubling of voltage
(2) non-constant resistance with time
(3) non-constant resistance with voltage or current Furthermore, the EMP response does not seem to be very affected by viscosity; and the EMP response is enhanced by increasing the dielectric constant of the solution while the electrophoretic mobility is inversely proportional to dielectric constant so EMP may be practiced at dielectric levels far exceeding those practicable with electrophoresis. Thus EMP in media with a dielectric constant up to 190 has been practical, e.g., in N-methylacetamide.

The migration rate in cm/sec of chemical species transported by EMP is markedly superior to the rates achieved with dielectrophoresis and electrophoresis having a significantly greater value in the semi-conductive range of values of conductivity.

It is thought that the EMP process relies on proton donor/acceptor interactions and electron charge transfer complexes for transport. See R. Foster, *Organic Charge-Transfer Complexes* (1969).

In practical terms, a key consideration in this process pertains to the use of a relatively nonconductive medium. Various different media and techniques may be used to achieve the requirements of the semiconductive ranges employed. Conduction can be carried out in solids, semisolids, such as gels, as well as in the gaseous phase, aerosols, foams and liquids. Also, combinations of these are practical as are melts, high temperature melts, pseudo crystals (para crystals and mesomorphic materials), ices, slushes, glasses, plastics, fibers, filaments, porous materials and powders. Ion exchange media, permaselective and membrane barriers, dialytic membranes, molecular sieves and specific ion source materials are suitable as supports or barriers. The process may be carried out continuously or by the batch technique.

Many substances are relatively dielectric; of these the nonpolar organics constitute a vast grouping. Some of these exhibit intermediate ranges of conductivity or are susceptible to appropriate adjustment of their conductive nature by addition of relatively small amounts of adjuncts. This may be likened to the process of doping or implantation used with solid-state devices. Other means may include irradiation, polarization interaction, injection or radioactive or charged particulates, photo activation, superposition of AC fields, magnetic fields or other energizing means. These energizing fields may be oriented at different angles with respect to the DC field. For example, an AC field superimposed upon the DC field used in this invention may be used to impart additional mobility to chemical species within a medium. Pulsed DC or the superimposition of pulsed DC may also be used. A relatively polar material can be used as the medium, such as aqueous solutions, by limiting the ionic content of the system to achieve the desired conductivity level. Also, suppressive substances can be added to a conductive system, desirable materials being those which exert a suppressive effect beyond the mere dilution effect which their presence contributes to the system. Further, the suppressive effect of nonpolar materials used in comixture with otherwise conducting systems offers a very general and useful approach to the control of conductivity. It is important to note that in regard to all of these techniques other factors may favor certain additional properties and characteristics of the materials employed appropriate for the nature of the application, such as miscibility, compatibility, toxicity, boiling point, melting point, reactivity, cost, removability, dialyzability and osmolality. A high dielectric constant material is often preferred due to its ability to maintain the charges formed in the system (involving solvation or interaction) or charges otherwise acquired or induced upon chemical species. The attainment of a controlled level of conductivity may be further controlled or adjusted by the simultaneous consideration of other system parameters, such as pH, physical state and temperature.

Mixed solvents may be used with the intermediation of a coupling agent, usually of a semipolar cosolvent nature. The term semipolar is used for a material which shows some conductivity, which will increase upon dilution with water (or other similarly polar material), and which will increase upon addition of a soluble ionic salt. Thus, in the present invention the solvation of a strongly ionic material into a nonpolar one by means of a semipolar material will generally produce only a minor conductivity increase, whereas the solution of the ionic material in the semipolar solvent alone may be moderately conducting. In effect, the nonpolar material may be viewed as suppressing the capabilities for moderate conduction to form a three-way system. The three-way system therefore comprises an inert base, a conductivity agent and a semipolar material, such as, respectively, xylene, ammonium bromide and dimethyl formamide. Further, a considerable increase in the amount of the semipolar solvent may only minimally improve the conductivity. The addition of a relatively small volume of a second type of semipolar solvent (a four-way system) can then effect a very substantial conductivity increase of the entire system. Neither co-solvent alone with the nonpolar material, without or including the solvated ionic material, will approach the conductivity level so achieved. This technique for augmenting the conductivity of essentially nonpolar materials forms a convenient working basis for the use of substances such as xylene, p-cymeme, mineral oil and chlorinated solvents. An illustration of a four-way system is xylene, ammonium bromide, dimethyl acetamide and dimethyl formamide.

The above effects also may be applied to systems which are not readily ionizable and the components determined by such factors as dielectric constant and proton donor capability of the solvating molecules. Whereas medium donor capability may give rise to solvated molecules, a high donor capability in a high dielectric system readily tends to preserve the ionic charges so created. Of particular use are media having dielectric constants above 10, which tend to maintain charges formed by protondonor acceptor exchange.

The media used in this invention are characterized by liquidity at or near room temperature, and sufficiently high boiling points to withstand the process heat. The boiling points are generally above 140° C., and preferably above 165° C. The media need not be capable of dissolving the chemical to which mobility is to be imparted, but solubility is preferable for separation of different molecular species.

This invention is further illustrated by the following examples directed to the separation of chemical species in the indicated media. The apparatus consisted of a high density polyethylene separation cell divided into two 15cc compartments; these being separated by a space containing a support bridge for a spanning support substrate. The cell was constructed to withstand and provide security from the high voltage fields and conductive leakage of media under such fields and the wide range of strong and corrosive solvent materials used herein. A platinum electrode in each compartment was connected to a DC power source generally operated at 1.25 ma. The power source was capable of metered operation at variable voltage levels in the ranges of 0–100 μa, 0–1 ma, and 0–10 ma, for threshold studies and operation of the processes described herein. A filter paper wick in each compartment was connected to opposite ends of the filter paper substrate which extended across the top of the cell. The filter paper was five cm wide by ten cm long and except where stated otherwise it was Whatman 3. Normally, the voltage drop in this system occurs substantially across the impregnated support, for example from 70% to 90% or more. The cell was enclosed by a transparent cover.

A suitable solvent can be selected from the class of low molecular weight glycols with a minor amount of an additive to increase conductivity. The following solvent systems are useful for relatively nonpolar dyestuffs as well as other soluble organic materials. The solvents listed were used for the separation of mixed chemical species, such as dyes, Mercurochrome, and sodium riboflavin phosphate, at the voltage and current shown. The term "stabilized" is used to indicate that the electrical characteristics reached the indicated values and remained constant for the few minutes (generally two to ten minutes) during which the separation process was completed.

| Example | Solvent Formulae | Electrical Characteristic (Stabilized) |
|---|---|---|
| 1 | 0.3 ml. water, 0.2 ml. Sorensen Buffer (pH 7.0), 24.5 ml. propylene glycol. The amount of water in this type of system should preferably not exceed about 2%. | 11 KV/ma |
| 2 | 2.0 ml. dimethyl acetamide, 1.0 ml. phenol, 25.0 ml. propylene glycol | 8 KV/ma |
| 3 | 2.5 ml. formamide, 22.5 ml. propylene glycol. | 5.5 KV/ma |

Example 3 is excellent for dye resolution of the following mixture: saframin 0, toluylene red (neutral red) and sodium riboflavin phosphate. This media is also useful for separation of members of the rhodamine dyestuff family.

Unlike conventional ionic-transport processes the mobilization of metal derivatives is not readily achieved, even when the metal derivatives are soluble in the media. However, by adjustment of the media and electrical characteristics in accordance with this invention a very fine resolution is obtained, which illustrates a new mode of operation as described herein. By suitable modification of the above solvent systems, metal ion movement may be made practical, as in the following systems. Examples of suitable metal ions are $Co^{++}$, $Cu^{++}$, $Ni^{++}$ from salts, such as the chlorides and nitrates

| Example | Solvent Formulae | Electrical Characteristic (Stabilized) |
|---|---|---|
| 4 | 10 ml. dimethyl formamide, 15 ml. propylene glycol | 10 KV/ma |
| 5 | 10 ml. dimethyl formamide, 15 ml. propylene glycol, 1 ml. triethanolamine | 8 KV/ma |

Another approach is to use dithizone derivatives of metals such as cobalt, copper and nickel in solvent systems such as (4) and (5) above.

As ester based nonaqueous system is also satisfactory as illustrated below. In place of the cellosolve in the medium, other related compounds can be used, such as hexyl cellosolve, methyl carbitol, cellosolve acetate, and carbitol acetate.

| Example | Solvent Formulae | Electrical Characteristic (Stabilized) |
|---|---|---|
| 6 | 4 ml. formamide, 14 ml. cellosolve, 34 ml. dimethyl phthalate | 15 KV/ma |

The following examples show tailoring of the conductivity levels (doping) via nonaqueous salt methods and especially the additional influence of a second semipolar material wherein n-butanol S is a saturated solution of ammonium bromide in n-butanol. This medium is illustrative of a four-way system discussed above, and is useful for the separation of dyes and other compounds soluble therein.

| Example | Solvent Formulae | Electrical Characteristic (Stabilized) |
|---|---|---|
| 7 | 5 ml. n-butanol S, 30.5 ml. n-decanol, 2 ml. 1-methyl-2- | |

| Example | Solvent Formulae | Electrical Characteristic (Stabilized) |
|---------|------------------|----------------------------------------|
|         | pyrrolidinone    | 14 KV/ma                               |

The following solvent systems are useful for separation of metal ions and complexes; of the metal complexes, dithizones, nitroso B-napthol, pyrocatechol violet, rhodamine B, 8-hydroxy quinoline, and dibenzoylmethane derivatives were used.

| Example | Solvent Formulae | Electrical Characteristic (Stabilized) |
|---------|------------------|----------------------------------------|
| 8 | 30 ml. methoxy ethoxy ethanol + 30 ml. 1, 2-propanediol cyclic carbonate + 3 drops nitric acid (1:30 in $H_2O$) | 6.4 KV/1.25 ma |

The medium of Example 8 gave multizone resolution (5 minutes) with rare earth 8-hydroxy quinolinates such as Sc and Eu as well as other metals such as Ni. The heavy metal derivatives of dibenzoylmethane and rhodamine showed good to excellent movement whereas with heavy metal nitrates movement was very sparse and with hafnium (as chloride) not at all. Satisfactory mobility was also obtained for $Co^{+2}$, $Cu^{+2}$, and $Ni^{+2}$ (as chlorides).

In the previous example the nickel chloride gave three zones, with spot coloration of blue and violet. Such reproducible effects demonstrate the very great resolution of the technique. This also points to the formation of a series of metal complexes, such as by proton donor/acceptor exchange, and the ability of the technique to differentiate and resolve them. This unusual capability is evidenced by another situation where not only do multizones appear, but these appear as both (+) or (−) moving entities. Mobility rates of +2 cm/min were achieved with the following systems.

| Ex. | Solvent Formulae | Electrical Characteristic (Stabilized) |
|-----|------------------|----------------------------------------|
| 9 | 15 ml. methoxy ethoxy ethanol + 15 ml. 1,2-propanediol cyclic carbonate + 6 ml. isophorone + 3 drops nitric acid (1:30) | 6.8 KV/ma $Cu^{+2}$ (chloride) 3 zones (+ and −) $Fe^{+3}$ (chloride) 5–6 zones (+ and −) $Ni^{+2}$ (chloride) 3 zones (−) 6 min. run |
| 10 | 15 ml. methoxy ethoxy ethanol + 15 ml. 1,2-propanediol cyclic carbonate + 13 ml. ethylene carbonate +3 drops nitric acid (1:30) | 6 KV/ma $CO^{+2}$ (chloride) 2–3 zones (+ and −) $Ni^{+2}$ (chloride) 2–3 zones (+ and −) $Cu^{+2}$ (chloride) 4–5 zones (+ and −) 6 min. run |

The medium of Example 10 also provided excellent mobility for salts of europium, lutetium, thallium and ytterbium. The position, mobility rate, and character of the zones obtained are characteristic for the material within the system under given conditions. Thus, in the following system, nickel and cobalt (as chlorides) gave 1 to 2 zones respectively, whereas the mixture gave 3 zones corresponding to that of the individual metal constituents. Further, the zones had 3 colors with sharply distinguished pink and blue.

| Example | Solvent Formulae | Electrical Characteristic (Stabilized) |
|---------|------------------|----------------------------------------|
| 11 | 21 ml. 1,2-propanediol cyclic carbonate +9ml. methoxy ethoxy ethanol +8 ml. Γ-Butyrolactone +3 drops Nitric acid (1:30) | 7.8–7.6 KV/1.25 ma 6 min. run |

Another similar system resolves nickel and cobalt mixtures into pink and blue colored zones. This system is particularly fast with certain nonpolar dyestuffs giving 5 cm/min mobility rates at 7.5 KV levels. Operation at higher voltage levels would increase further the mobility rates:

| Example | Solvent Formulae | Electrical Characteristic (Stabilized) |
|---------|------------------|----------------------------------------|
| 12 | 21 ml. 1,2-priopanediol cyclic carbonate +9 ml. methoxy ethoxy ethanol +12 ml. bis (2-methoxy ethyl) ether +3 drops nitric acid (1:30) | 8.4–6.6 KV/1.25 ma |

The rare earth groupings as well as hafnium and zirconium represent the most difficult elements for resolution. Further, just as hafnium and zirconium form a particularly close pair, within the rare earths 3 major paired groupings are known. The following systems are useful for the transition and heavy metal categories; including salts of the rare earths and zirconium — hafnium elements, such as those having an atomic number of 21 and greater.

| Example | Solvent Formulae | Electrical Characteristic (Stabilized) |
|---------|------------------|----------------------------------------|
| 13 | 15 ml. 1,2-propanediol cyclic carbonate +15 ml. methoxy ethoxy ethanol +13 ml. ethylene carbonate +3 drops nitric acid (1:30) | 9.6–7.2 KV/1.25 ma 3 min. run |

Example 13 was successfully repeated with the medium substantially the same except that in each run the ethylene carbonate was replaced by one of the following: tetrahydrafurfuryl alcohol, isophorone, cellosolve, cyclohexanone, and 2-ethylhexyl chloride.

In a system comprising propanediol cyclic carbonate, nitric acid, methoxy methoxy ethanol and tetrahydrofurfuryl alcohol in proportions similar to those above at 500V and 100 μa, the dye saframin 0 moved readily, and an orange contaminant remained immobile. This is an example of the separation of components by reaching the threshold level for one compound in a mixture.

Acidification with an inorganic acid is not essential as the following example illustrates.

| Example | Solvent Formulae | Electrical Characteristic (Stabilized) |
|---------|------------------|----------------------------------------|
| 14 | 12 ml. 1,2-propylene glycol + 3 ml. dichloro acetic acid + 16 ml. ethoxy ethoxy ethanol | 14 KV/1.5 ma |

Also, media containing bases such as triethanolamine or γ-picoline in place of an acid, have the capability for the separation of metals.

The application of this invention to organic compounds is further illustrated by the following systems used for the separation of sulfa drugs, sulfamerizine, sulfaquanidine and sulfamethazine.

| Example | Solvent Formulae | Electrical Characteristic (Stabilized) |
|---|---|---|
| 15 | 20 ml. methoxy ethoxy ethanol + 12 ml. 1-methyl 2-pyrrolidinone + 0.8 ml. dichloracetic acid | 5.8–5.0 KV/1.25 ma 4 min. run |

The latter system, though found to be slow, was able to yield differential zones with the dyestuff family of rhodamine 5 G, 6 G, and B, as well as a mixture.

The following media gave high resolution of the above dyes in 20–25 seconds and mobility rates in excess of 12 cm/min.

| Example | Solvent Formulae | Electrical Characteristic (Stabilized) |
|---|---|---|
| 16 | 24 ml. 1,2-propanediol cyclic carbonate + 12 ml. ethylene diacetate + 6 ml. salicylaldehyde + 3 drops nitric acid (1:30) | 13.2 KV/0.8 ma |

The following two very fast related formulae approach 20 cm/min mobility rates with excellent resolution:

| EXAMPLE | SOLVENT FORMULAE | ELECTRICAL CHARACTERISTIC (Stabilized) |
|---|---|---|
| 17 | 24 ml. 1,2-propanediol cyclic carbonate + 12 ml. ethylene diacetate + 6 ml. salicylaldehyde + .4 ml. ammonium bromide (saturated in methoxy ethoxy ethanol) | 14.2 KV/ma |
| 18 | 24 ml. 1,2-propanediol cyclic carbonate + 12 ml. ethylene diacetate + 6 ml. salicylaldehyde + 2 ml. ammonium bromide (saturated solution methoxy ethoxy ethanol) + 2 ml. tributyl phosphate + 4 drops tetramethyl ammonium hydroxide (about 25% in methyl alcohol) | 13–12.6 KV/ma |
| 19 | 10 ml. tris-chloride (0.14m) + 90 ml. water (sucrose to 67%) | 2 KV/ma |

It is noted that urea or propylene glycol in such systems, in concentrations to several molar, doesn't alter the conductivity although it may aid the mobility of protein molecules. These substances act as a diluent or suppressant and are useful in water solutions for biochemical separations of substances such as proteins and enzymes. Albumin mobility in such systems can exceed that of glycol soluble dyestuffs, as shown below by the data for migration from the origin.

| EXAMPLE | SOLVENT FORMULAE | ELECTRICAL CHARACTERISTIC (Stabilized) |
|---|---|---|
| 20 | 16 ml. tris-chloride (.03M) + 40 ml. propylene glycol + 50 ml. glycerin | 6 KV/2 ma Whatman #1 Albumin 1¼ – 1-½" Soluble dye 3/4" 6 min. run |
| 21 | 10 ml. tris-chloride buffer (0.03M) + 40 ml. propylene glycol + 50 ml. methylcarbitol | 7.2 KV/2ma Cellulose acetate Paper |

As discussed further below, the foregoing systems can be improved in speed and degree of resolution using initiators, suppressants and/or stabilizers.

Operation of this process was also carried out by adding a sample to a bed of a gel made from agar, silica, and gelatin. This procedure has been used to separate dyes, proteins and other types of organic compounds. The media and electrical characteristics were similar to those described in the preceding examples. Bulk separations have also been carried out in a column with powdered minerals or cellulose supports.

A very useful system for non-polar substances, which has resolved isomers of methyl naphthalene and provided good resolution of Rhodamine B and 6G and food dyes is:

21 ml. propylene cyclic carbonate
9 ml. methoxy ethoxy ethanol
12 ml. tetrahydrofurfuryl alcohol
3 drops nitric acid (1:30)

In the preceding formulae, use was made of various types of compounds to perform or provide different important functions. For illustrative purposes, a number of these are selected for arrangement into several categories according to some of their common formuation functions. However, these categories are not rigidly defined limitations for the use of any compounds and some fall equally well across several category boundaries. Thus, dimethyl phthalate is an example of a good suppressant although it also functions as an inert base if used as the base media. Further, it may act to insolubilize or limit mobility or influence other factors, thereby enhancing resolution. Water is useful for a fairly active solvent with moderate proton donor capabilities and high dielectric constant. This latter feature tends to maintain the charges once established. However, water is generally less useful as a major constituent at the higher voltage levels in non-externally cooled systems due to its low boiling point.

Table I

| Inert Media-base | Conductivity agent |
|---|---|
| Characteristic: | Perchloric acid |
| minimal conductivity | dichloracetic acid |
| solvent, inert carrier, | formamide |
| solution limiter. | ammonium bromide |
| p-cymene | pyridazine iodide |
| mineral oil | nitric acid |
| n-decanol | mercaptoacetic acid |
| 1-octanethiol | Active Media base |
| xylene | Characteristic: |
| Inhibitors (suppressant) | slight conductivity with tendency |
| Characteristic: | to enhance conductivity of neutral |
| negative conductivity | media base. |
| influence. | potent solubilizer, solvent |
| tributyl phosphate | 2-chloroacetamide |
| dimethyl phthalate | dimethyl formamide |
| triacetin | N,N,-dimethylacetamide |
| 2-ethyl hexyl chloride | 1-methyl-2-pyrrolidone |
| Neutral media-base | dimethyl sulfoxide |
| Characteristic: | ethylene cyclic carbonate |
| slight to poor conductivity | 2,5-hexanedione |
| with tendency for active | Modifying agents |
| change in conductivity with | isophorone |
| dilution solvent, potent | nitrobenzene |
| solubilizer, coupling agent. | salicylaldehyde |
| Γ-butyrolacetone | 4-hydroxy-4-methyl-2-kpentanone |
| 1,2-propanediol cyclic carbonate | ethylene diacetate |
| propylene glycol | Γ-picoline |
| 2-phenoxy ethanol | o-dichlorobenzene |
| 2-ethyl, 1,3-hexanediol | |
| tetrahydrothiophene 1,1-dioxide | |
| methoxy ethoxy ethanol | |
| Very Active Media | |
| Characteristic: | |
| strong conductivity influence, proton donor | |
| solvent action and scidity-alkalinity | |
| diethyl ethyl phosphonate | |
| N-cyclo-hexyl-2-pyrrolidone | |
| bis (2-methoxy ethyl) ether | |
| Hexa methylene phosphoric triamide | |
| amino ethyl piperazine | |
| imino bis propylamine | |
| 2,2'-imino diethanol | |
| 2-amino ethanol | |
| triethylene tetramine | |
| triethanolamine | |
| mercaptopropionic acid | |
| mercaptoacetic acid | |

A starting point for developing and choosing a solvent media for particular chemical species is to determine those media which stabilize or are compatible with the species and which exert a good to excellent partition coefficient in a standard chromatographic technique for the species on the substrate to be used at various pH. The conductivity level is then adjusted for use in this process by adding the solvent as a major constituent to a compatible media base system which has a properly adjusted conductivity or, the conductivity of the solvent can be tailored to form a media base system by the use of the types of agents described in Table I. Mobility is normally achieved at about 1.25 ma, which generally exceeds most threshold current levels. Further adjustment may be necessary to initiate or refine the mobility of the species by the adjustment of the composition of the system as indicated above. For example, adjustment may be made by the use of complexing agents, modifying agents, similar solvents as determined by chromatographic screening, by pH adjustment and less active substrates (such as teflon).

The compounds listed herein are representative of a much vaster possible grouping of like or related materials useful as solvents, cosolvents, coupling agents with moderate, strong or nil effects on conductivity; many form complexes and metal adducts substantially modifying the effective properties of the compounds or materials involved.

These materials are often used in comixtures to achieve their desired combined properties. Such formulations, aside from their electrical properties, achieve a very broad scope of applicability for different classes of molecular species.

The following list of substances may be considered in three main categories, given below. Other factors to be considered are a larger liquidity range, and dielectric constant, low viscosity, water compatibility and miscibility and strong donor/acceptor influence or neutrality:

1. The major grouping has boiling points at or above 160° C. which are liquid at or near room temperature. Generally they have good solvent action.
2. A number of the compounds listed have boiling points in the 130°–160° C. range, or melting slightly above room temperature. These are often used in lesser percentages to modify systems. Also, they often can be liquified with a minor amount of cosolvent.
3. The remainder are modifying agents, whose melting points may be substantially higher and which are used in solution with other media.

Based upon physical characteristics, chromatographic screening tests, and the media adjustment techniques described herein, the following compounds are representative of the type of media component useful in this process:

TABLE II

Alcohols 2-aminoethanol 2-ethylaminoethanol
2,3-epoxy-1-propanol ethylene dinitrile tetraethanol
2,2-iminodiethanol dl-menthol
2 mercaptoethanol
furfuryl alcohol
tetrahydro furfuryl alcohol
2,2'-oxydiethanol
2,2'2"-nitrilotriethanol
1,1'1"-nitrilotri-2-propanol
1-phenylethanethiol
2,2'-(phenylimino)diethanol
1,3-propane dithiol
thiodiethanol
4-pyridine propanol
2-nitro 1-propanol
2-nitro-1-butanol
2-amino-2-(hydroxymethyl)-1,3-propanediol
geranoil
2-methylamino ethanol
2-methyl-2-nitro-1,3-propane diol
2-(hydroxymethyl)-2-nitro-1,3-propanediol
phenol
aziridine ethanol
hydroxy ethyl piperazine
piperazine ethanol
2-Dimethyl amino-2-methyl-1-propanol
sorbitol
glucose
sucrose
ethylene glycol
propylene glycol
dipropylene glycol polyethylene glycol
thiodiethylene glycol
1-octanethiol
4-hydroxy-4-methyl-2-pentanone linalool
linalool oxide

Ethers, esters dibutyl phthalate phenyl acetate dibutyl fumarate dimethyl phthalate diethyl phthalate ethyl lactate ethyl malonate di iso octylazelate
di-2-ethyl hexylazelate methyloleate
tri (n-octyl) mellitate
tri (n-decyl) mellitate
acetyl tributyl citrate tributyl citrate
ethylene diacetate
tetra hydro furfuryl oleate
tris (chloro ethyl) phosphate
2,2,4-tri methyl-1,3-pentanediol diisobutyrate
di ethoxy ethyl phthalate
methoxy ethyl ricinoleate
glycerol monoacetate
di n-hexyl adipate
glycerol tributyrate
butane diol dicaprylate
ethylene glycol dibenzoate
di ethylene glycol dibenzoate
di propylene glycol dibenzoate
polyethylene glycol (200) dibenzoate
tri ethylene glycol diacetate
bis (diethylene glycol mono ethyl ether)

5-hydroxy-2-(hydroxymethyl)-4H-pyran-4one
2-(2-ethoxy ethoxy) ethanol
2-[2-(ethoxy ethoxy) ethoxy] ethanol
2-(2-butoxy ethoxy) ethanol
1-[[ [2-(2-methoxy-1-methylethoxy)]-1-methyl ethoxy]]-2-propanol n-butanol
1,3 butanediol
1,4-butanediol
2-(2-butoxy ethoxy) ethanol
2-butoxyethanol
2-(2-methoxy ethoxy) ethanol
2-methoxy ethanol
3-methoxy-1-butanol
2-butoxy-ethanol
2-ethyl hexane-1,3-diol
t-butanol
iso-amylalcohol
caprylic alcohol
decanol dehydroisophytol
glycerin
dehydrolinalool thioglycerol 3-chloro-1, 2-propanediol
2-amino-1-butanol
2-amino-2-ethyl-1,3 propanediol
2-amino-2-methyl-1-propanol
tributyl phosphate
triethyl phosphate
tricresyl phosphate
triphenyl phosphate
tri(2-ethyl hexyl) phosphate
tributoxy ethyl phosphate
o,o,o-triethyl phosphorothioate
diethyl ethylphosphonate
dibutoxy ethyl sebacate
2-ethyl hexylchloride
bis [2-(2-methoxy ethoxy) ethoxy] ether
bis (2-methoxy ethyl) ether
2-methoxy ethyl acetate
ethoxy ethyl acetate
2-(2-butoxy ethoxy) ethylacetate
diethylene glycol monomethylether
diethylene glycol monoethyl ether
ethylene glycol monoethyl ether acetate
ethylene glycol mono ethyl ether acetate
ethylene glycol monohexyl ether
diethylene glycol monoethyl ether acetate
diethylene glycol monomethyl ether
ethyl cyanocetate
3-acetyl-3-chloropropyl acetate
butyl chloroacetate
butyl lactate
butyl stearate
di tetra hydro furfuryl adipate TABLE II-continued phthalate
bis (2-ethyl hexyl) adipate
1,2-bis (2-chloroethoxy) ethane
bis (2-chloroethyl) carbonate
bis (2-methoxy ethyl) phthalate
di mercaptodiethyl ether
glycol di mercaptoacetate
di methyl thiodipropionate
tri methylol ethane tri (3-mercapto propionate)
penta erythritol tetra (3-mercaptopropionate)
bis (2-chloro-isopropyl) ether
glycerol triacetate
glycerol tripropionate
1,2/1,3-glycerol diacetate
hexyl acetate
ethylmethyl carbamate
hydroxy ethyl acetate
phenyltrimethoxy silane
trimethoxy trimethyl mercapto silane
dimethylpoly siloxanes
1,2-bis (2-methoxy ethoxy) ethane 2-(ethoxy ethoxy) ethylacetate dibenzyl ether Amides formamide N,N-dimethyl acetamide
2-chloroacetamide
ureau
1,1,3,3-tetra methyl urea
acrylamide
cyanamide
N,N-bis (2-cyanoethyl) formamide
2-cyanoacetamide
2-furamide
N-2 hydroxy ethylformamide
N-ethyl p-toluene sulfonamide
N-ethyl-o-toluene sulfonamide
N-2-hydroxy ethylacetamide
methane sulfonamide N-(2-methoxy ethyl) acetamide
N,N'-methylene bis acrylamide
N-ethyl formamide hydracrylonitrile
imino diacetonitrile
p-methoxyphenyl acetonitrile
glutaronitrile
succinonitrile
picolino nitrile
nicotinonitrile
benzonitrile
ethylcyanoacetate
4-chloro-3-hydroxybutyronitrile
3,3'-[2,2-Bis(2-cyano ethoxy methyl)-trimethylane dioxyl diproplenitrile Aldehydes, ketones, thiones, miscellaneous compounds 2'-hydroxyacetophenone
salicylalehyde
fenchone
4-anisaldehyde
o-chlorobenzaldehyde
isophorone
cyclohexanone
2-piperidone 2-furaldehyde
1-methyl-2-pyrrolidinone
2,6-dimethyl-4-heptanone
p-cymene
o-dichlorobenzene
o-nitrotoluene
nitrobenzene
isosafrole
choline
n-ethyl morpholine
2,6-dimethyl morpholine
hexamethylene tetra-amine
2-picoline-1-oxide
tetramethylammoniumhydroxide
tetrabutylammonium hydroxide N-methyl formamide
thioacetamide
picramide
hexamethyl phosphoric triamide
formamideine acetate Lactones, lactams, diones, and carbonates ethylene cyclic carbonate -butyrolactone
2,5-hexanedione 6-hexanolactone 1,2-propanediol cyclic carbonate
oxohexamethylenimine
2,3-butanedione
ethylene trithiocarbonate
propiolactone
2-piperidone
n-butyl carbonate
4,4,4,-trifluoro-1,2 thienyl-1,3-butanedione
2,4-pentanedione
dipropyl carbonate
2,4-pentanedione Nitriles ethylene dinitrile tetracetonitrile
pimelonitrile
3,3-thiodipropionitrile
3,3-oxydipropionitrile phenylacetonitrile
o-methoxy benzaldehyde
tetrahydroionone
pyridazine iodide
decahydronapthalene
diphenyl methane
durene
d-limonene
turpentine
mineral oil
dichlorophenyl trichlorosilane octadecyltrichlorosilane diphenyl dichloro silane
epibromohydrin
1,1,2,2-tetrabromoethane
1,2,3,4-tetrahydronapthalene
tetrachloroethane
1,2,4,-trichlorobenzene
indene
pyrrolidinone
1-butyl-2-pyrrolidinone
1-cyclohexyl-2-pyrrolidinone Basic Compounds - and amines, hydroxides, oxides, sulfides, hydrates, alcoholates, heterocyclics iodine chloride-iodine systems
sulfur chloride-iodine systems
benzyltrimethylammoniumhydroxide
betaine hydrate 3-methyl piperazine
4-methyl piperidine
4-methyl thiazole
2-methyl thiazole
2-methyl tetrahydro furan
tetrahydrothiazole
1,4 oxathiane

TABLE II-continued

| | |
|---|---|
| tetramethyl guanidine | 1,2,3-azimidobenzene |
| 3-ethyl-4-methylpyridine | 2-amino-1,3-bis (2-ethyl hexyl)-5-methyl hydropyrimidine |
| 5-ethyl-2-methylpyridine | 3,5 lutidine |
| hexamethylene imine | Acidic Media |
| tetrahydrothiophene 1,1-dioxide | methane sulfonc acid |
| dimethyl sulfoxide | dichloroacetic acid |
| imino-bis-propylamine | mercaptoacetic acid |
| triethylene tetramine | 3-mercaptopropionic acid |
| butyraldoxime | propionic anhydride |
| 2-amino-4-methyl thiazole | lactic acid |
| N-propyl sulfoxide | 2-chloropropionic acid |
| N-butyl sulfoxide | propionic acid |
| alpha picoline | sulfoacetic acid |
| beta picoline | trichloroacetic acid |
| quinoline | (ethylene dinitrol) tetra-acetic acid |
| 1,2-diazine | trimethylacetic acid |
| aminoethyl piperazine | picric acid |
| 2-methyl-5-ethyl pyridine | camphoric acid |
| N-hydroxy ethyle piperidine | hexanoic acid |
| 3-ethyl-4-methyl pyridine | picramic acid |
| 4-ethyl pyridine | cyanuric acid |
| 2,4 lutidine | picrolinic acid |
| 2,6-dimethyl pyridine-n-oxide | Lewis acids |
| Lewis bases | |
| p-toluenesulfonic acid | 2,2'2" nitrilo triethanol hydrochloride |
| trifluoroacetic acid | semicarbazide hydrochloride |
| amino imino methane sulfonic acid | ammonium formate |
| amino ethane thiol sulfuric acid | ammonium thiocyanate |
| 2-amino ethyl hydrogen sulfate | ammonium nitrate |
| perchloric acid | ammonium bromide |
| sulfamic acid | lithium bromide |
| phosphoric acid | lithium iodide |
| sulfuric acid | morpholine oleate |
| nitric acid | lithium nitrate |
| Salts | lithium hydroxide |
| betaine hydrochloride | cesium acetate |
| choline chloride | cesium chloride |
| hydroxylammonium acetate | cesium carbonate |
| hexadecyltrimethyl ammonium bromide | cesium salicylate |
| quanidine nitrate | potassium iodide |
| tetrabutyl ammonium iodide | poly vinyl benzyl trimethyl ammonium chloride |
| tetra ethylammonium bromide | hydroxylammonium acid sulfate |
| tetra methyl ammonium bromide | Lewis salts |
| 1,1,1 trimethyl hydrazonium iodide | |
| acetylcholine bromide | |
| acetylcholine iodide | |
| aminoguanidine nitrate | |
| 6-amino-3-indazolinone dihydrochloride | |
| cyanuric chloride | |
| guanidine acetate | |
| guanidine hydrochloride | |
| amino guanidine bicarbonate | |

Formulation of the EMP media is fundamental. It has been found that compounds or mixtures with a large liquidity range are particularly suited for use in EMP, especially those liquids with a glassy or vitreous structure. These compounds or mixtures apparently have an inherent structure which facilitates regulation of proton donor/acceptor properties and electron charge transfer, as well as providing the advantage of low evaporation. It is sometimes practical to use high boiling point liquids because the practice of EMP at or above higher threshold currents does generate some heat. Media with higher or lower melting and boiling components may be used for special applications.

Components used in EMP media formulation should have a number of characteristics if they are to be maximally useful. Water and solvent miscibility are often desired, and is general solvent action, availability, and thermal, shelf, chemical and electrical stability. Superior solvent activity is not always desired. It is feasible to limit or cause differential movement when two or more transportable chemical species are present in the media by using media components which are poor solvents for one or more species. Below is a list of additional compounds useful for their solvent action or their ability to mediate such properties in other materials. Also included and tracer agents which will be discussed more fully hereinafter.

TABLE III

| HYDROXY, ETHER COMPOUNDS | |
|---|---|
| 1,2,4-Butanetriol | 2-(Ethyl thio)ethanol |
| O-Tertbutyl phenol | Ethynyl cyclohexanol |
| 2,2-Bis(hydroxy methyl) propionic acid | Ethynyl cycloheptanol |
| | Ethynyl cyclooctanol |

TABLE III-continued 2,3-Butanediol
1,4-Butanediol diglycidyl ether
2-Butene-1,4-diol
2-(n-Butylamino)-ethanol
Butylhydroxytoluene
2-Butyne-1,4-diol
Cetyl Alcohol
Chloral
Cyanoethyl sucrose
Dichlorotriethylene glycol
ihydroxy acetone
2,2-Diethyl-1,3-propanediol
2,5-Dihydroxy methyl pyrrole
1,3-Dimercapto-2-propanol
2,3-Dimercapto-1-propanol
Dimethoxy tetra ethylene glycol
2,3-Dimethyl-2,3-butanediol
Dimethylol propionic acid
2,2'-Dithiodiethanol
Dodecyl alcohol polyoxyethylene ether
O-Ethyl phenol
Anilino ethanol
Amylether
Benzene thiol
Benzyl alcohol
Benzyl butyl ether
N-Benzyl ethyl ether
2-Benzyl oxythanol
4-Bromodiphenyl ether
N-Butyl phenyl ether
N-Butyl diethanolamine
1-Chlor ethyl cellosolve
1-Chloro-3-pentanol
4-Chloro cyclohexanol
6-Chloro-1-hexanol
O,M,P-Cresols
O,M,P-Chlorophenols
6-Chloro thymol
2-Cyano ethanol
Cinnamyl alcohol
Cedrol
Cyclo hexanol
1,4-Cyclo hexane di methanol
Decanediol
2,3-Dibromo-1-propanol
1,3-Dichloro-2-propanol
2,3-Dichloro-1-propanol
2,4-Dichloro phenol
1,3-Dichloro-2-methyl-2-propanol
2-Imidazoline-1-ethanol
5-Indanol
2-(Iso propyl thio)ethanol
Lanolin alcohols, acetylated
5-Methyl-1,3-dioxane-5-methanol
2-Nitro-2-ethyl-1,3-propanediol
2-Nitro-2-methyl-1-propanol
O-Nitro anisole
O-Nitro phenol
2-Methyl-1-phenol-3-butyne-1,2-diol
M-Nitrobenzyl alcohol
2-Nitroethanol
1,5-Pentanediol
Pentaerythritol
P-Pentoxyphenol
Phenethyl alcohol
Sec. Phenethyl alcohol
1-Phenyl-1,2-ethanediol
Poly ethoxy ethylated(1-20) oleyl alcohols
Polyethoxylated lanolin(5+) alcohols
Polyethoxylated (75) lanolin
Polyethoxylated (9) acetyl lanolin alcohol
P-butoxy phenol
Polyclycols
2-Methyl-2,4-pentanediol
2-Methyl cyclohexanol
3-Methyl cyclohexanol
4-Methyl cyclohexanol
2-Methyl-1-phenyl propanol-1
2-Methyl-1-phenyl propanol-2
P-(methyl thio)phenol
2-Nitro diphenyl ether
Glycidol
Guaiacol
1,2,6-Hexanetriol
Hydroxy acetone
3-Hydroxy camphor
2-Hydroxy cyclodecanone
2-Hydroxy ethyl ether
2-Hydroxy ethyl hydrazine
N-Hydroxy ethyl morpholine
2-(Hydroxy methyl)-2-ethyl-1,3-rpoapnediol
1-(Hydroxy methyl)-5,5-dimethyl hydantoin
2-Hydroxy ethyl methacrylate
1-(B-Hydroxy ethyl(2-methyl-2-imidazoline
4-Hydroxy-3-methyl-2-butanone
2-Hydroxy-3-methyl cyclopenten-1-onehydrate
3-Hydroxy-2-methyl-4-pyrone
5-Hydroxy oxindole
3-Hydroxy piperidone
2-Hydroxy pyridine
5-Hydroxy-4-octanone
Iodopropylidene glycerol
N-Methylol-2-pyrrolidone
Diethanol sulfide
α,α-Dimethyl phenethyl alcohol
2,4-Dimethyl phenol
2,6-Dimethyl phenol
4,6-Dinitro-o-cresol
2,4-Dinitro phenol
2,6-Dinitro thymol
2,3-P-Dioxanediol
Diphenyl ether
2,6-Di-tert-butyl-p-cresol
2,6-Di-tert-butyl phenol
2,4-Di-tert-pentyl phenol
6,6-Dimethyl bicyclo 3,1,1 hept-2-ene-2-ethanol
Dodecyl alcohol
P-Dodecyl phenol
1-Dodecane thiol
1,2-Ethane dithiol
Ethane thiol
1-Ethoxy naphthalene
O-Ethoxy phenol
Glycerol di methyl ether
3-Hydroxy propionitrile
3-Hydroxy propylene oxide
1,6-Hexanediol
Hexyl cellosolve
D-Methoxy phenol
DL-α-Methyl benzyl alcohol
5-Methyl-2-isopropyl phenol
2-Methyl-1,2-3-propanetriol
Polymethyl alkyl siloxanes
Pyrrole-2-ethanol
Pyrrole-2-methanol
Stearyl alcohol
2,5-Tetra hydrofurandimethanol
1,2,3,4-Tetra hydro-2-napthol
Tetra hydro pyran-2-methanol
Tetra hydro-2)2)5-trimethyl-5-cinyl furfuryl alcohol
Tetrahydropyran-2-methanol
2,2,4,4-Tetramethyl-1,3-cyclobutanedi
Tetra ethylene glycol
2-Thenyl alcohol
Thiobenzyl alcohol
2,2'-Thiodiethane thiol
2,2-Thiodiethane thiol
Triethylene glycol dimethyl ether
1,1,1-Trichloro-2-propanol
1,1,1-Trichloro-2-methyl-2-propanol (& hydrate)
1,1,-Trimethylol ethane
Trimethylolpropane
Tris(hydroxy methyl)nitromethane
Toluene-3,4-dithiol
Aldol
1-Amino-2-propanol
3-Amino-2-propanol
3-Amino-2-butanol
2-amino thiophenol
O,P-Toluenethiol
3-Cyclohexene-1-methanol
3-Cyclohexene-1-dimethanol
3-Nitro-2-butanol
2-Nitroethanol
2-Nitro-1-propanol

AMIDES, IMIDES

TABLE III-continued

1-Octanol
1,2,3-Propanetriol
1-Phenyl-1-propanol
3-Phenyl-1-propanol
2,2,4,4-Tetra methyl-1,3-cyclobutanediol
P-1,1,3,3)-Tetra methyl butyl phenol
Thio phenol
M-Thio cresol
Crown ethers
Trimethylol amino ethane
1-(2-Hydroxyethyl piperozine
P-Hexyl phenol
P-Hexyl oxyphenol
O-Phenyl phenol
2,4,5-Trichlorophenol
2,4,6-Trichlorophenol
2,2,2-Trichlor-1-ethoxy ethanol
2-Vinyl oxyethyl ether
2,4,6-Trinitroresorcinol
N,N-Dibutyl formamide
2,2-Dichloroacetamide
N,N'-Dicyclohexyl carbo diimide
Diethyl formamido malonate
N,N-Diethyl Tso nico-tinamide
N,N-Diethyl nicotinamide
N,N-Diethyl nipecotamide
N,N-Diethyl-1-piperazine carboxamide
N,N-Dimethyl acetoacetamide
N,N-Dimethyl nicotinamide
3,3-Dimethyl glutaramide
2,4-Dihydroxybenzamide
N,N'-Dimethyl oxamide
3,5-Dinitro benzamide
2,3-Epoxy-2-ethyl hexanamide
N-Ethyl acetamide
Ethyl acetamido acetate
N-Ethyl acrylamide
N-Ethyl maleamic acid
3-Ethyl-3-Methyl glutaramide
N-Ethyl methacrylamide
N-Ethyl nicotinamide
N-Ethyl propionamide
Ethyl oxamate
Fluoroacetamide
P-Nitrobenzamide
Oxamic acid
Oxamide
α-Phenyl butyramide
Phenyl formamide
N-Phenyl succinimide
Phthalamide
N-Polyoxy ethylene fatty acid amides
Propionamide
Pyrazinamide
Stearamide
Succinimide
Succinic diamide
Sulfabenzamide
Sulfacetamide
Sulfamide
N-Sulfanyl stearamide
N,N,N',N'-Tetra ethyl phthalamide
N,N,N',N'-Tetra ethyl fumarimide
N,N,N',N'-Tetra methyl carbamide
Thiobenzamide
Thionicotinamide
O,P-Toluamide
2,2,2-Trifluoroacetamide
Trimethylacetamide
Valeramide
N-2-(Hydroxy ethyl) succinimide
2-Furamide
Lactamide
N-Methyl benzamide
N-Methyl diacetamide
M-Methyl-N-1-naphthyl acetamide
N-Methyl-2-phenyl acetamide
N,N,N',N'-Tetra methyl glycinamide
N,2,2-Trimethyl propionamide
4-Acetamino-2,2,6,6-tetra methyl piperidino-1-oxyl
2-Acetamido-3-butanone
4-Acetamido butyric acid
4-Acetamidothiophenol
2-Acetamido thiazole
2-Acetoacetamido-4-methyl thiazole
Adipamide
N-Allyl methacrylamide
6-Amino nicotinamide
Anthranilamide
Azodiacarbonamide
N-Bromoacetamide
2-Bromo-2-ethyl Iso valeramide
N,n-Butul acrylamide
N-Butyramide
Iso-butyramide
Chloral formamide
Cinnamamide
Diacetamide
N,N'-Diallyl tartardiamide
Fumaramide
1-Glutamide
Glutaramide
Heptamide
N,N-Hexamethylene formamide
Hexamethyl phosphorour triamide
2,2,2-Trichloroacetamide
N-Hydroxy acetamide
2-Hydroxy ethoxy acetamide
N-(2-Hydroxy ethyl)-phthalimide
N-(Hydroxy methyl)-nicotinamide
N-Hydroxy succinimide
5-Hydroxy valeramide
Iodo acetamide
Iso-nicotinamide
Iso-nipecotamide
N-Iso propyl acrylamide
N-Iso propyl salicylamide
N-Lauryl methacrylamide
Maleamic acid
Maleimide
Maleondiamide
N-Methyl acetamide
N-Methyl acrylamide
N-Methyl maleimide
2-Methyl malonamide
N-Methyl nicotinamide
N-Methyl propionamide
N-Methyl 2,2,2-Trifluoroacetamide
Methyl-2,2,2-Trichloroacetamide
1-Naphthaleneacetamide
4-Acetamido-2,2,6,6-tetra methyl piperidine
N-Butylacetamide
tert-Butyl carbazate
Diacetone acrylamide
N,N-Diallyl formamide
Dibutyl cyanamide
N,N-Dibutyl propionamide
N,N-Diethyl acetamide
Diethyl acetamido malonate
N,N-Diethyl butyramide
N,N-Diethyl formamide
N,N-Diethyl propionamide
N,N-Diethyl-m-toluamide
N,N-Dimethyl dodecanamide
N,N-Dimethyl propionamide
N,N-Dimethyl thioacetamide
N,N-Dimethyl thioformamide
N,N-Dimethyl valeramide
3,5-Dinitro-o-toluamide
N,N-Diphenyl acetamide
N,N,-Dipropyl acetamide
N,N-Dipropyl decanamide
N,N-Dipropyl propionamide
N-Ethyl maleimide
Ethyl methyl carbamate
Hexanamide
Hexaethyl phosphorus triamide
2-Hydroxyethyl carbamate
2-Chloro ethyl trichlor acetate
2-Chlor ethyl chloro acetate
6,9-Diamino-2-ethoxy acridine lactate
Di isopropyl adipate
Dimethyl methyl phosphonate
2-Di isopropylaminoethyl-p-amino benzoate
Di iso-butyl carbonate
Dibutyl sulfite
Dibutyl (+) - tartrate
Dimethyl maleate

TABLE III-continued 2,2,5,5-Tetra methyl-3-pyrrolin-1-gloxy-3-carboxamide
1-Naththaleneacetamide
Phenyl carbonimide
Acetamidine acetate
P-Acetamido benzaldehyde
P-Acetamido benzoic acid
N-[2-(Acetamido)-imino] diacetic acid

ESTHERS, CARBONATES

Allylidene Diacetate
Bis(2-Ethyl hexyl)sebacate
Bis(2-Ethoxy ethyl) sebacate
Bis(2-Ethyl hexyl) phthalate
N-Butyl oleate
Butyl nitrite
Glucose-1-phosphate
Glycol diformate
Iso butyl carbonate
Iso-pentyl nitrite
Iso-propyl salicylate
Methyl cyanoacetate
Methyl cinnamate
Methyl decanoate
Methyl myristate
Methyl octanoate
Methyl palmitate
Methyl salicylate
Methyl stearate
Monostearin
Monolein
Methyl abietate
Methyl acetoacetate
Methyl benzoate
Methyl trichlor acetate
N-Octyl nitrate
Phenyl carbonate
Polyoxy ethylene stearate
Isopropyl salicylate
N-Propyl nitrate
Phenyl acetate
Propyl benzoate
Tetra hydrofurfuryl nicotinate
Tetryhydro furfuryl acetate
Tetra nitro methane
2,2,2-trichloro ethyl carbamate
2-Imidozolidone
Indole-3-cyclohexanone
L-Methone
4-Methoxyacetophenone
Methyl benzophenone
O-Methyl anisole
4-Methyl acetophenone
α-Methyl cinnamaldehyde
2-Methyl piperazine-N,N'-dicarboxaldehyde
N-Methyl pyrrole carboxaldehyde
N-Morpholino carboxaldehyde
Nicotinaldehyde
5-Nitro salicylaldehyde
Nitroso salicylaldehyde
2-Octanone
1-Phenyl-2-propanone
Phenetole
Picolinoaldehyde
1-Piperazine carboxaldehyde
1,4-Piperazine dicarboxaldehyde
N-Piperidino carboxaldehyde
Piperonal
Propiophenone
2-Pyridone
4-Pyridone
Pyridine-2-carbaldehyde
Pyridine-3-carbaldehyde
O-Aminophthalhydrazide
Benzothiazole N,N'Bis (3-amino propyl)-piperazine
Bis (2-Ethyl hexyl) orthophosphoric acid
2,2-Bis (ethyl sulfonyl) butane
1,8 Bis(dimethylamino)-naphthalene
Butyl sulfone
Bis(2-ethyl hexyl) hydrogen phosphate
Butyl disulfide Dimethyl malonate
Diethyl oxalate
Dibutyl oxalate
Diethyl adipate
Dipropyl adipate
Dibutyl adipate
Diethyl sebacate
Di iso-butyl adipate
Di-N-butyl sebacate
Dimethyl phosphite
Ethyl trichloro acetate
Ethylene(mono) thio carbonate
Ethyl-2-pyridine carboxylate
Ethyl anthranilate
Ethyl acetoacetate
Ethyl benzoate
2-Ethyl hexyl acetate
Ethyl dichloroacetate
Trilauryl phosphite
Trilauryl trithiophosphite
Trimethyl-3,3',3''-nitrilotripropionate
Trimethyl phosphate
Triethyl orthopropionate
Triethyl phosphite
Tri Isopropyl phosphite
Tri butyl borate
Tri(2-Tolyl)phosphite
Tetra hydrofurfuryl propionate

KETONES, ALDEHYDES

2-Acetyl cyclohexanone
P-Acetaldehyde
Anisole
P-Butyraldehyde
Butyrophenone
P-Chlorophenetole
Cinnemaldehyde
1,2-Cyclohexanedione
1,2-Cyclodecanedione
3-Cyclohexene-1-carboxaldehyde
1,3-Dichloro-2-propanone
Decanone
2,5-Dimethyl cyclohexanone
3,5-Dimethyl-5-ethyl-2,4-dione
N-Formyl hexamethyleneimine
Hexachloroacetone
2,4-Imidozolidine dione
Pyrrole-2-carbaldehyde
Thiophene-2-carbaldehyde
Tribromoacetaldehyde
Veratraldehyde
O,P-Vanillin
O-Phthaldialdehyde
1-Phenyl-3-pyrazolisinone
2-Heptanone
Pentaerythritol diformal
Methyl-2-thienyl ketone
Cyclododecanone
Azacyclotridecanone

HETEROCYCLICS, ACIDS, AMINES (& SALTS), MISCELLANEOUS SUBSTANCES

N-Acetyl morpholine
2-Acetyl pyrrole
2-Acetyl thiophene
Acridan
Acridine
Acridine orange
Acridine yellow
Acriflavine
Allyl thiourea
1-Allyl pyrrole
2-Allyl pyrrole
Amino acids
9-Amino acridine
3-Amino acridine
Dimethyl acid pyrophosphate
2,5-Dihydrothiophene 1,1-dioxide 2,3-Dihydro-4-pyran
2,4-Dimethyl-3-ethyl pyrrole
2,3-Dimethyl-4-ethyl pyrrole
2,5-Dimethyl pyrrole
3,4-Dimethyl-5-sulfanilamido iso oxazole, salts
Di Phenyl sulfide
Di isopropanolamine
Dichloro propionic acid
N-Nitroso diethylamine
1-Nitrosopiperidine

TABLE III-continued

Tert-butyl disulfide
9-Chloroacridine
4-Chloromethyl-1-acridine
2-Chloropyridine
4-Chloropyridine
A,B-Cyclopentamethylene tetrazole
3,6-Diamino acridine
1,8-Diamino-p-methane
1,2-Diazole
Dihydroacridine
1,2-Dihydro-3,6-pyridazinedione
2,3-dihydrofuran
3,4-Dihydro-1(2H)-naphthalenone
Methyl phenyl sulfide
1-Methyl-1-phenyl hydrazine
3-Methyl sulfolane
N-Methyl pyrrole
Nepatolactone
Nitrocyclohexane
O-Nitrophenol
2-Nitropyrrole
O-Nitroanisole
2-Nitrofuran, 3-Nitrofuran
1-Nitrosopiperidine
Oxypolygelatin
Pantoic acid-α-lactone
1,5-Pentamethylene-tetrazole
O-Phenetidine
Phenyl hydrazine
Phenyl mercuric borate
P-Phenetidine
4-(3-Phenyl propyl)-pyridine
Phenyl phosphonous dichloridate
Phenyl phosphoro dichloridate
Phenyl phosphone thioic dichloride
Phenyl phosphoric dichloride
Piperine
Pyridine-1-oxide
Pyridazine
1-Chloronaphthalene
2-Chloroquinoline
3-Cyclohexapropionic acid
Caprylic acid
1-Chloro octane
Chloropicrin
Caproic acid
O-Chloroaniline
Cumene
2,4-Dichloropyrimidine
3,6-Dichloropyridazine
3,7-Dichloroquinoline
2,5-Dihydro-2,5-dimethoxy furan
N,N-Dimethyl cyclohexylamine
1,4-Dimethyl piperizine
1,4-Dinitroso piperazine
2,3-Dichlorodioxane
1,5-Dichloropentane
Dibenzylamine
N,N-Dibutyl aniline
Dipentylamine
1,3-Dioxepane
1,3-Dioxolane
2-(1,3-Dioxolane-2-yl) pyridine
4,4'-Dithiomorpholine
3,4-Dimethyl furazan
Di iso amglamine
Di butyl amine
4-Methyl morpholine
N-Methyl-P-nitroaniline, O-nitroaniline
2-Methyl quinoline
2-Methyl pyridine
3-Methylpyridine
4-Methyldioxolane
Methyl urethane
α-Methyl styrene
1-Nitropropane
2-Nitropropane
1-Nitrobutane
1-Nitrohexane
Nitro trichloro methane
N-Octyl nitrate
4-Phenyl-1,3-dioxane
3-Propyl rhodanine
Propyl disulfide
Dibutyl butylphospho
α-Glucose-1-phosphoric acid
Gluconic acid
Guar Gum
Indole
Imidazole
Iminodiacetic acid
Hexamethylene imine
3,5-Lutidine-N-oxide
2-Lactoyl oxypropanoic acid
Lithium acetate
Lithium perchlorate
1-Methyl imidazole
2-(Methyl thio)benzothiazole
2-Methyl glutaronitrile
Methyl isobutyl ketoxime
Pyrimidine
Pyrrole
Quinoxaline
Safrole
Stearic acid
Trimethyl sulfoxonium iodide
1,2,3-Trimethyl benzene
1,2-Epoxycyclododecane
N-(3-Amino propyl)-2-pyrrolidinone
N-(3-Amino propyl)-morpholine
Acetonaphthane
4-(2-Amino ethyl)morpholine
N-(3-Amino propyl)-morpholine
N-Butylaniline
Butyl sulfide
Benzylamine
Benzedrine
2-Benzyl pyridine
1-Bromonaphthalene
Butyl benzene
1-Bromo-2-iodobenzene
1-Bromo-3-iodobenzene
Butyl nitrite
Cyclododecane
1,5,9-Cyclododecatriene
Cyclododecene
1,2-Cyclohexane dicarboxylic anhydride
Cedrene
O-Diethyl benzene
3,4-Dimethylpyridine
Dibutylamine
O-Diethylbenzene
1-Ethylnaphthalene
2-Ethylnaphthalene
3-Tehylrhodanine
1-Ethylpyrrole
Ethyldiethanolamine
O-Ethyltoluene
Fluorosulfuric acid-antimony pentafluoride
Isopentyl nitrite
Heptanoic acid
Lactonitrile
Lithium oleate, palmitate, stearate
O-Iodotoluene
P-Isopropyltoluene
1-Iodonaphthalene
1-Iodo octane
Iso pentyl nitrite
2-Methyl benzothiazole
2-Methyl benzoxazole
1,2-Methylenedioxybenzene
1-Methyl naphthalene
2-Methyl naphthalene
2-Methyl-2-nitropropane
N-Methyl-N-nitrosoaniline
Methoxyacetic acid
Aluminum lactate
Amino phosphonic acids
Bismuth ethyl camphorate
Calcium carbamate
Calcium borogluconate
Calcium palmitate
Calcium stearate
Calcium galactogluconate bromide
Circumin
Cinnamonitrile
O-Diacetyl benzene
Decahydroquinoline
1,4-Dichlor-2-nitro benzene
1,2-Dichloro-4-nitro benzene
1,1-Diethyl urea
Dimethyl phosphite
Diphenyl selenide
Diphenylimidazalon-sulfonated

TABLE III-continued

Propyl sulfide
Propyl sulfone
Piperidine
Valeric acid
Trimethylene sulfide

MISCELLANEOUS SUBSTANCES

Acridine red
Acridine iso thiocyanate
Acriflavine
Aesculin
Allantoin
Phenyl ethylene oxide
1-Phenyl propane
Primuline
1,3-Propane sultone
Isopropyl benzene
N-Propyl nitrate
1,4-Pyrone
Pyruvic acid
Safranin
Sulfonyldiacetic acid
Sulfuriodide
Tetrabutyl ammonium petchlorate
Tetrabutyl ammonium fluoroborate
Tetracutyl ammonium bromide
Tetraethyl ammonium perchlorate
Tetraethyl thiuram sulfide
Tetraethyl ortho silicate
Tetraethyl ortho titanate
1,1,3,3-Tetraethyl urea
Tetra isopropyl ortho titanate
1,1,3,3-Tetraethoxy propane
Tetraethyl tin
Tetrahydrofurfuryl oxy-tetrahydropyram
1,2,3,4-Tetrahydro isoquinoline
Trioctylphosphine oxide
Trioctyl phosphine
Tri-N-pentyl amine
Vasoflavin
Vinyl carbazoles
Zinc oleate Flourescamine
N-Iodoacetyl-N'-(5-sulfo-1-naphthyl)-ethylene diamine
N-Iodoacetyl-N'-(8-sulfo-1-naphthyl)-ethylene diamine
Lutidines
2-Methyl-2-thiazoline
O-Methyl toluidine
Metrizaminde
Nile Blue
Neutral red
Neutral violet
2,3,4,5-Tetramethyl pyrrole
N,N,N',N'-Tetramethyl-1, 8-naphthalene diamine
2,3,5,6-Tetramethyl piperazine
2,2,4,4-Tetramethyl-1,3-cyclo-butadiamine
1,2,3,4-Tetramethyl benzene
3,3',5,5'-Tetramethyl benzidine
Tetranitro methane
Tetrocyanoethylene
Thiamorpholine
Thiolactic acid
3,3'-Thiodi propionic acid
Thiophthene
1,4-Thioxane
Thioflavine
O,M,P-Toluidine
Triazio benzene
Tri-N-butyl amine
Tri iso butyl amine
Tri-N-butyl phosphine oxide
Tri butyl phosphine
3,5,5-Trimethyl-2,4-oxazolidine dione
Trimethyl sulfonium iodide
Trimethyl sulfoxonium iodide
Trimethyl amine N-oxide, hydrate
1,3,5-Tri nitro benzene
2,4,6-Trimethyl pyridine
Trichloromethyl phosphonic acid As part of the methodology which may be used to categorize the materials such as those listed herein they may be titrated with distilled water and their conductivities obtained. The dilution/conductivity curve so obtained indicates the rate of change of conductivity with dilution as well as the diminishing point or plateau levels of conductivity achieved within reasonable dilution means which helps characterize the materials as to the several categories discussed herein, such as very active solvents, active solvents, etc. The following data illustrates the application of this technique (resistances are given in milliona of ohms). The very low plateau of resistance at the indicated dilution levels establishes that dichloroacetic acid and mercaptoacetic acid are in the category of very active media. The somewhat higher plateau of ethylene carbonate and 2,5-hexanedione place them in the category of active media. By such a method a convenient rating scale can be established for evaluation of different media. This technique assists in tailoring media to a desired conductivity value by observation of resistance values at different levels of dilution.

Often even partial miscibility with water is sufficient to indicate the range of activity or character to be expected. Further, these studies are extended by titration against materials other than water. Thus, for example dichloracetic acid, formamide and thiodiethylene glycol were used. These then represent a different solvent miscibility capability and profile. Of these agents, the formamide has a very high dielectric constant and greater conductivity than water, whereas the thiodiethylene glycol's conductivity was in the range of the water used and also achieved the level of conductivity of the water when a drop of water was added; that is, upon only slight dilution with the water. The conductivity changes so produced by dilution with nonaqueous materials were further characterized by observing changes in plateau levels so produced by addition of a minor quantity of secondary solvents which may be water. This helps to relate the influence of secondary solvents such as the active or very active type (or inert type for suppressant activity) to the conductivity profile. Such effects are variable or characteristic for the diluted agents to which the secondary diluent is added.

| SAMPLE | INITIAL RESISTANCE, 0.3 ml. | RESISTANCE WITH .05 ml. WATER ADDED | RESISTANCE WITH 1 ml. WATER ADDED |
|---|---|---|---|
| dichloroacetic acid | 100 | 0.042 | 0.001 |
| mercaptoacetic acid | 1 | 0.050 | 0.004 |
| ethylene carbonate | 0.2 | 0.20 | 0.065 |
| 2,5-hexanedione | 7 | 2.2 | 0.060 |

Further, the conductivity titration curves may be studied with a particular conductivity-valued diluent which may already be an ionizeo or higher conductivity system. For example, the dilution of hydroxy compounds and ethers with fairly conductive aqueous ammonium nitrate solution and acetic acid may be cited. The comparison was made where both latter systems had equivalent conductivities. Of the compounds 1,3-butane diol, 2,2-methoxy ethoxy ethanol, 2-oxydiethanol bis (2-methoxy ethyl) ether, sorbitol (40% aqueous solution) and sorbitol (57% aqueous solution) by volume, the dilution of the aforementioned aqueous conductive solutions by the latter compounds generally shows a similar decrease in conductivity over the titration range although certain definite curve shapes were derived. Thus, the relative activity and suppressant profile of the various diluants became evident. With this technique, the substantial difference with bis (2-methoxy ethyl) ether is readily evident. Also differences were noted in the effects of aqueous sorbitol at various concentrations, as compared to the nonaqueous materials, upon the ionized ammonium nitrate solution which effects were otherwise somewhat less pronounced than upon a dilute acetic acid solution. Further, the various systems may be studied as they affect equilibria characteristics, ionization and/or formation data for the materials of interest and at various pH's. A large compendium or library of data may be prepared for these various possibilities in order to achieve a lessened empirical basis for conditions of system selection for use. As a result of this invention an already established broad table is given of basic solvent systems from which future screening can be made to develop media for use with particular species.

As illustrated by the above examples and the lists of chemicals, the process of this invention comprises separating or mobilizing chemical species which are conveniently on a support such as filter paper in a medium of low conductivity across which a high voltage is impressed. The media-base comprises one or more compounds, for example, inorganic or organic compounds such as glycols, ethers, esters, diones, lactones, amides, nitriles, alcohols and water. An agent may be added to the medium to adjust its conductivity and such agent may be selected from the group consisting of water, acids, bases and salts. The voltage used in the process is within the range of about 50 to 25,000 volts/cm. At very high voltages, and particularly with volatile or gaseous substances, cooling may be required. The preferred range is about 200 to 3,000 volts/cm, and in this range the process can be carried out without external cooling. The conductivity of the medium is preferably adjusted to provide a current density in the range of about from 0.2 to 100 microamps/sq. cm. based on the area of, for example, filter paper as a substrate. The preferred range is 1.4 to 54 microamps/sq.cm. For bulk work and with external cooling, current densities above 100 microamps/sq. cm. can be used. TThe transport medium, after appropriate adjustment of its conductivity, is subjected to a sufficiently high voltage at a low current level (at about the threshold level) to induce separation of the chemical species therein at a rate of about 1 cm/sec. to about 0.25 cm/min. In the above examples, at the conditions indicated, no external cooling was required.

Refinement of media formulation techniques can lead to resolution improvement in the separation of given components by EMP. For example, the media of 5 ml. propanediol cyclic carbonate, 5 ml. propylene glycol, 2 ml. N-methylacetamide and 0.4 ml. tetrahydrofurfuryl alcohol allows the resolution of rhodamine B and 6G of examples 16 above in considerably less than the 3.6 cm. required in example 16. The utilization of resolution improvement to shorten separation distances makes is possible to minimize diffusional effects.

It is possible to improve resolution generally according to the following procedure. A suitable solvent is found for the chemical species to be transported. The nature of the chemical species to be transported is then analyzed in terms of its proton donor/acceptor properties. The donor/acceptor properties of a number of chemical species are catalogued in the literature. E.g., V. Gutmann, *Coordination Chemistry in Non-Aqueous Solutions* (1968). A component should then be added to the media which will interact in a proton donor/acceptor interaction with the chemical species. In many instances the proton donor/acceptor properties of chemical species are not catalogued, or are complex. In such cases it is possible to determine the type of media components that will improve resolution by testing the system through the simple technique of addition of a very strong proton donor to one sample and then a very strong proton acceptor to another. If the strong donor increases the mobility (rate of movement) of the compound, donors of varying strength are then tested to determine which provides the greatest improvement in mobility and resolution. An analogous procedure is followed if the strong proton acceptor increases the mobility rate of the chemical species. The addition of a component which can interact with the chemical species to be transported by proton donor/acceptor interaction seems to facilitate initial mobilization of the chemical species. The dielectric constant of the media is then adjusted if necessary to a moderately high level. It may also be necessary to correct for electrical instability of the media by addition of a compensating component as detailed above.

As an additional aspect of this invention it has been determined that improved tailoring of the semiconductive media also permits, for certain chemical species, exhibition of an EMP resonse observable with the unaided eye at relatively low voltages and reduced power levels, as compared to the high voltage, high power processes described above. Voltages below 50 v/cm and even less than 20v/cm on conventional support media have been utilized. For example, one can achieve EMP transport at power levels as low as $3 \times 10^{-6}$W. to $1.7 \times 10^{-5}$W. with voltages of 2 to 4 volts at 1.5 to 4.2 $\mu$A. over several centimeters of No. 1 Whatman filter paper. This represents EMP operation at potentials of several millivolts per centimeter at tenths of microwatts per square centimeter. The limit on low voltage EMP is the level at which electrical diffusivity comes into play. It has also been found that certain agents will act to reduce the threshold current of a chemical species.

A media system is modified to allow low voltage EMP response and to reduce threshold current in much the same manner as it is modified for resolution improvement. Specifically, iniciators and mobilizers are added. Initiators are compounds which act to reduce the threshold current of a given chemical species, and mobilizers are compounds which act to increase the mobility (transport rate) of a given chemical species. There is some overlap between the classes of compounds useful as initiators and those useful as mobilizers, that is, some compounds will act both as initiators and as mobilizers.

In general, materials which will interact on a proton donor/acceptor level with the chemical species to be transported and high dielectric constant materials are useful as initiators and mobilizers. Examples of compounds which are often useful both as initiators and mobilizers are N-methylacetamide and salicylaldehyde.

With the use of initiators, threshold currents may be adjusted as low as 0.2 to 0.002 $\mu A/cm^2$, and EMP may be carried out at these currents at slower but still effective mobility rates with voltages as low as 0.05 to 10v/cm. The voltage level of 0.05 v/cm represented a practical minimum during experimentation because voltage effects on this order inherent to the system were encountered. Overall, considering both high voltage and low voltage EMP, the EMP voltage range may be 0.05 to 25,000 v/cm, with power levels as low as $1.2 \times 10^{-9}$ to $5 \times 10^{-5} W/cm^2$.

The following examples illustrate the manner in which media, suitable for EMP transport according to the criteria of semiconductivity and compatability with chemical species described in connection with high voltage EMP above, are modified with initiators to reduce threshold current.

| EXAMPLE | SOLVENT FORMULAE |
|---------|------------------|
| 22 | 7 ml. propylene glycol, 3 ml. diacetone alcohol (mobilizer, also enhances resolution), 2.2 ml. N-methylacetamide (high dielectric constant material, acts as initiator and mobilizer), 1.3 ml. formamide (same). |
| 23 | 21 ml. propanediolcyclic carbonate, 9 ml. methoxyethyl ethanol, 12 ml. tetrahydrofurfural alcohol, 3 drops $HNO_3$ diluted 1:3 with water. |

The media of example 22 above has been used to separate rhodamine dyes, and also to separate vitamin $B_{12}$ and sodium riboflavin phosphate mixtures.

The media of example 23 was used to separate rhodamine B and 6G in less than 0.5 cm. The tetrahydrofurfural alcohol acted to embrace the mobilization of the compounds magnifying molecular differences. Without this component the two species showed almost equivalent motion over several centimeters.

As further examples, the media of example 23 can be altered to increase its conductivity by the dropwise addition of conductivity, initiator or mobilizing agents (A.) to obtain the electrical values (B.) and power levels (C.) set forth in the table below.

| (A.) Agent | (B.) Electricl Values for EMP run (on 4 × 1 cm Filter Paper) | (C.) Total EMP Power Level in Microwatts |
|---|---|---|
| Nitric acid (1:30 in water) | 4V, 4.2$\mu$a | 17 |
| Ammonium bromide (Sat'd. in glycol) | 10V, 1.1$\mu$a | 11 |
| formamide | 10V, 1.2$\mu$a | 12 |
| N-Methyl Acetamide | 20V, 2$\mu$a | 40 |
| N-Methyl formamide | 10V, 4.1$\mu$a | 40 |
| Hexamethyl phosphoric triamide | 10V, 3.5$\mu$a | 35 |

The accomplishment of EMP at low voltages with accompanying low power levels has important ramifications in that EMP under such conditions would be compatible with living organisms. Voltage, power and threshold current levels appropriate for low voltage EMP exist in living organisms and consequently are clearly tolerated by them. Thus the EMP technique of formulation of semiconductive media may be effected within a living organism to control or study chemical substances in physiologically functional systems.

The voltage necessary to the EMP process may be supplied by potential differences existing naturally in an organism and merely applied to the appropriate site, or may be imposed from an outside source.

It is well known and recognized in the prior art that potential differences exist within living organisms naturally. Also, in connection with the experimentation leading up to the present invention, it was found that a voltage reading on the order of tenths of volts or millivolts with a current of microamps or slightly less was generated across the phase boundary between two immiscible or partially immiscible liquids in certain instances. Not all phase boundaries produced this junction effect; for liquids, partial solubility in each other seems to correlate with the effect to some extent. The junction effect may be modified by use of a permeable membrane between the phases. Propanediolcyclic carbonate and water form different phases and exhibit this junction effect. It is believed that juxtaposition of liquids in the cells of living organisms could give rise to a liquid junction effect providing sufficient voltage for the effectuation of EMP. Such effects appear to be amenable to modification by EMP media formulation techniques.

The process of EMP media formulation may be carried out in conjunction with an externally applied voltage, as well as with one existing naturally within an organism or portion thereof, to effect an EMP response. Some evidence already exists, for example, of improved bone and other tissue healing or growth in the presence of an applied voltage. See Lavine et al., Electric Enhancement of Bone Healing, 17 Science 1118 (March 1972). Such effects could be enhanced by application of the desired chemical species. For example, the initiators or dielectric constant modifiers for transport of biochemical species described herein could be applied to facilitate or enhance an electrophysiological response such as transport or orientation of the appropriate materials across a bone break.

More generally, given voltages and current levels within living organisms, the procedure of media formulation of the present invention could be used to construct or modify within the organism appropriate semiconductive media for enhanced transport of physiologically significant chemical species. For example, EMP media formulation techniques could be used to speed reparative or other chemical species to injured portions of the body. EMP media formulation might also be useful with respect to the application or retention of drugs. EMP might be used to effect or control natural processes on a humoral, intercellular, or even intracellular level.

In the preparation of media within an organism, toxicity of the media components and other aspects of compatability with the physiological system would be of key importance. Considerations of toxicity would include considerations of irritational, inhibiting and denaturing characteristics. In selecting chemical materials useful for in vivo EMP work, the particular tissue or function to be modified must be taken into account. Even nitriles can find utility in such work, e.g., 2-cyanoethanol is relatively non-toxic as well as non-irritating and non-absorbing dermally.

As an example, if it were desired to utilize an agent intravenously in mammals (including humans) which is well tolerated in fair concentrations, and which should contribute amide but not urea character, either lactamide or nicotinamide may be selected. For liquid or low melting N-alkylamides or N,N-dialkyl amides, often of high to very high dielectric constant, analogues such as N-ethyl nicotinamide or N,N-diethylnicotinamide may be considered. A number of related compounds, e.g., dibutyl formamide, N-cyclohexyl-formamide, diethyl nipecotamide, or N-(2-hydroxyethyl) lactamide, might be useful.

In addition to these examples, a listing of agents is given for use in formulating buffers with minimal impairment of sensitive biological systems. Also, a brief listing is given of other representative agents sufficiently tolerated to be generally useful for biological work. Additional criteria for this latter group include low melting point, good liquidity range, water solubility, other solubility, solvent activity, inertness or functionality, etc.

TABLE IV

Biologically Compatible Buffer Agents and Zwitterionic Buffers

| | |
|---|---|
| cyclohexyl aminoethane sulfonic acid | N, N-bis (2-hydroxy ethyl glycine) |
| cyclohexyl aminopropane sulfonic acid | N'-2-hydroxy ethyl piperzine-N'-2-ethane sulfonic acid |
| N'-2-hydroxy ethyl piperazine-N'-2-propane sulfonic acid | piperazine-N,N'-bis (2-ethane sulfonic acid) |
| imidazole | N-tris (hydroxy methyl) methyl glycine |
| 2-N-(morpholino) ethane sulfonic acid | N-tris(hydroxy methyl) methyl-2-amineothane sulfonic acid |
| morpholino propane sulfonic acid | tris (hydroxy methyl) methyl aminopropane sulfonic acid |

TABLE V

Other Representative Materials Suited for Use in EMP Media in Biological Systems

| | |
|---|---|
| ε-acetamidocaproic acid | farnesol |
| L-α-acetamido-β-mercaptopropionic acid | fructose |
| acetamido phenol | D-gluconic acid δ-lactone |
| acetanilide | glutathione |
| allantoin | glycerophosphoric acid |
| alantolactone | 2,6,10,15,19,23-hexamethyl tetracosane |
| i-allyl-2,5-dimetholy-3,4-methylene dioxybenzene | 3-hydroxy-2-butanone |
| n-amyl butyrate | 2-hydroxybenzyl phosphinic acid |
| anhydromethylene citric acid | N-(2-hydroxyethyl)palmitamide |
| B-L-arabinose | 5-hydroxy-2-hexenoic acid lactone |
| arabitol | 2,6,10,15,19,23-hexamethyl-2,6,10,14,18,22-tetracosahexene |
| arachidonic acid | |
| benzylacetate | |
| 1,3-bis(hydroxy methyl) urea | 15-hydroxy pentadecanoic acid E-lactone |
| bis(2-ethylhexyl) 2-ethyl-hexylphosphonate | 5-hydroxy-2 (hydroxy methyl)-4-pyrone |
| ethoxy (10–20) glucose | |
| ethyl linoleate | 3-hydroxytrimethyldodecanoic acid, 3,7,11 |
| ethyl levulinate | ichthymall |
| 3-ethyl-1-hexanol | isoascorbic acid |
| 2-ethyl-2-methyl succinimide | iso-eugenol |
| 2-ethyl sulfonyl ethanol | inositol hexaphosphoric acid |
| ethylene glycol diacetate | isopropyl myristate |
| 1-ethynyl cyclohexanol | |
| eugenol | |
| iso-valeric acid | |

TABLE V-continued

Other Representative Materials Suited for Use in EMP Media in Biological Systems

| | |
|---|---|
| isovaleramide | |
| kojic acid | |
| lactobionic acid | citric acid |
| linoleic acid | |
| lipoic acid | tetrazole |
| methylal acetamide | Diethyl ethylphosphonate |
| methylnicotinate | N,N-diethyl iso-valeramide |
| γ-Methyl-α,β-N-methyl pyrrolidinone | N,N-diethyl-m-toluamide |
| 1-methoxy-4-propenyl benzene | 2,2-dimethyl-1,3-dioxolane-4-methanol |
| P-methoxy benzaldehyde | 2,6-dimethyl-m-dioxan-4-ol acetate |
| P-methoxy benzyl alcohol | |
| myristyl alcohol | dimethylpolysiloxane |
| 3,4-(Methylene dioxy)benzaldehyde | 2,3-epoxy-2-ethyl hexanamide |
| nicotinamide scorbate | ethyl phenyl ether |
| nicotinic acid monoethanolamine | O-ethoxybenzamide |
| 2-nitro-2-propyl-1,3-propanediol | propoxy (10–20) glucose |
|  | pentaerythritol chloral |
| octanoic acid | pentaerythritol tetraacetate |
| oleic acid | 3-pentanone |
| oils, natural | 3-phenoxyl-1, 2-propanediol |
| orotic acid | phenoxyacetic acid |
| N-(pantothenyl)-B-aminoethanethiol | polyolyethylene-(20)-sorbitan monooleate |
| Pantothenic acid | phenylbutyramide, α- |
| cacoa butter | 2-phenyl-2-hydroxy propionamide |
| E-caprolactam | 2-phenyl-6-theophylline & salts |
| choline salts | |
| piperidinium salts | O-thiocresol |
| poly(ethylene glycol)-p-nonyl phenyl ether | thujic acid |
| polyoxyethylene stearate | tiglicamide |
| polyvinyl alcohol | tocopherols, tocols |
| polyvinyl pyrrolidone | 2,2,2-trichloroethanol |
| N-polyoxyethylene fatty acid amides | triethylene glycol |
|  | 3,5,5-trimethyl-2,4-oxadolidinedione |
| 6-propylpiperonyl butyl diethylene glycol ether | undecylenic acid |
| 3-pyridine ethanol | veratrole |
| pyrrolidinone, 2- | viologens |
| polyethylene glycol-p-iso octyl phenyl ether | vital stains |
|  | valerolactone |
| steroids, natural and derived, e.g., ex-lanolin | vitamins K, A, & derivatives |
| salicylamide | wetting agents |
| sorbic acid | |
| tannins | |
| cis-terpinhydrate | |
| tetrahydro-3-furanol | |
| tetrahydrofurfuryl alcohol polyethylene glycol | |
| 3,7,11,15-tetramethyl-2-hexadien-1-ol | |
| 2,6,10,14-tetramethylpentadecane | |
| tetraethylene glycol dimethyl ether | |
| thiamine, sales & derivatives | |

EMP media components may be applied to an organism through known techniques, including injection and local profusion.

EMP in living organisms or in tissues may be operated at threshold currents on the order of 0.002 $\mu A/cm^2$ or higher, at voltages of 0.3 v/cm or higher. If slower EMP response is acceptable for a particular use, thresholds of 0.0005 $\mu A/cm^2$ may be utilized with voltages as low as 0.05 v/cm.

Related to the use of EMP in biological systems is the use of EMP to mobiolize biochemical species including high threshold ones as proteins -- globulins, enzymes, polypeptides, nucleic acids, steroids, lipids, lipoproteins and fatty acids. Proteins and other biochemical compounds are susceptible to thermal and chemical degradation, and are commonly handled in aqueous solution, often in chilled, buffered electrolyte solution. However, water as a major component in EMP media has the disadvantages of forming electrolytic solutions and of being rather evaporative. Thus special attention has been given to the adaptation of high water content systems to EMP usage, and also to the application of EMP to proteins and related substances in nonaqueous systems. Since the activity of biochemical compounds is linked to their structural integrity and sensitivity, an additional aim has been formulation of a versatile set of media which preserve this activity.

The general technique for formulation of an aqueous EMP media for protein transport involves reducing the conductivity of water by addition of a suppressant, adjusting the dielectric constant by addition of a high dielectric constant material if necessary, and adding initiators and/or mobilizers to beneficiate the movement of the proteins.

As disclosed above, it has been found that a number of compounds will suppress the conductivity of water to varying extents, thereby alleviating the problem of high conductivity in aqueous media. These compounds also function as miscible protein solvents. The conductivity suppression results are set out in the form of an example below.

EXAMPLE 24

Various protein-compatible solvents were combined with water (volume ratio = 16/9). Pure solvents were used when possible, as the trace contaminants in commercially available materials can affect conductivity suppression. (This is illustrated by the values given for compounds (7) and (18) below which are the same substance obtained from two different sources.) Relative values of conductivity suppression as compared to the conductivity of water were:

| (1) | thiodiethylene glycol | 2.2 |
|---|---|---|
| (2) | 2,6-dimethyl morpholine | 2.6 |
| (3) | methoxy ethoxy ethanol | 2.6 |
| (4) | 2-pyrollidone | 2.7 |
| More strongly conductivity suppressing compounds are: | | |
| (5) | δ-butyrolactone | 3.3 |
| (6) | sorbitol | 3.8 |
| (7) | 1,3-butanediol | 3.6 |
| (8) | propylene glycol | 3.6 |
| (9) | dimethyl formamide | 3.6 |
| A group of increased strength suppressants are: | | |
| (10) | dimethyl acetamide | 4.8 |
| (11) | tetrahydrofurfuryl alcohol | 4.6 |
| (12) | butoxy ethoxy propanol | 5.0 |
| (13) | 6-hexanolactone | 5.0 |
| (14) | oxydiethanol | 5.4 |
| (15) | diacetin | 5.6 |

The truly potent class of suppressants for water may be represented by:

| (16) | 2-[2-(ethoxy ethoxy) ethoxy] ethanol | 8.3 |
|---|---|---|
| (17) | 1-[[2-(2-methoxy-1-methyl ethoxy)]-1-methyl ethoxy]-2-propanol | 10 |
| (18) | 1, 3 butylene glycol | 12 |

Selection of a suitable suppressant solvent should take into account the effect of the suppressant on protein migration. Thus compounds (10), (11) and (13) above may beneficiate protein mobility, whereas (3), (4), (9), (14) and (18) may be less potent in this regard.

Additional solvents for biochemical compounds include alcohols such as methyl carbitol, phophonates such as diethyl ethyl phosphonate, lactones such as 6-hexanolactone and sugars.

Solvent compatibility with the substrate is another consideration. With improper solvent selection, the solvent may attack the substrate resulting in altered porosity, structure collapse or similar effects. Proper solvent selection in media formulation permits use, for example, of ion-exchange of "thinlayer" plates, as well as cellulose derivative films such as the nitrate or acetate, or agarose, acrylamide or silica gels impregnated with EMP media.

The excessive use of potent suppressants may result in a system with internal resistance so high that substantial resistive heating results, especially where high threshold current operation is indicated. Thus, selection of the less potent suppressants is often satisfactory. The Tc requirements of proteins and related substances are often in the range of 4.6 ma/50 $cm^2$ or more on a cellulose substrate as opposed to 1.2 ma/50 $cm^2$ or less for most other compounds.

Reducing the water content of EMP media as described above may alter the dielectric constant of the media. This change may be offset, with resulting reestablishment of the high dielectric constant desirable for EMP, by addition generally of very high dielectric constant components. Examples of suitable materials for this dielectric constant adjustment include hydroxy ethyl formamide, N-methyl formamide, formamide, N-methyl acetamide and related compounds. Generally, N-alkyl and N-aryl amides are useful. Often these compounds, especially when of only commercial purity, will tend to increase the conductivity of the media, thereby opposing the suppressant mechanism. Such conductivity contribution may be used to compensate for an overly high internal resistance caused by a strong suppressant.

High threshold values of biochemical species may be advantageously reduced, and the mobility of the species in EMP increased, by the use of initiators and mobilizers. Many proteins were found to be particularly susceptible to the influence of proton acceptor substances in increasing mobility, but were relatively indifferent to mobilization by proton donor molecules. Initiator substances, though in relatively low concentration, contribute susbstantially to the lowering of threshold current, and if they also act as mobilizers, to the enhancement of species mobility. For proteins, initiators may be used to bring threshold levels down from 4.6 ma/50 $cm^2$ to 3.4 to 1.0 ma/50 $cm^2$ (20$\mu$A/$cm^2$) with voltages in the 50 to 25,000 v/cm range. Typical initiator substances, mobilizers, and worthwhile solvents are: nitrobutanol; 3-acetyl 3-chloropropylacetate; salicylaldehyde; N-methyl-acetamide; boric acid; phenols; guaiacol; fumaric and barbituric acids; piperazine; furfural; tributoxy ethylphosphate; $\beta,\beta,\beta$-trichloro-t-butyl alcohol; dimethyl-1,3-dioxolane-4-methanol; 2-ethyl sulfonyl ethanol; tetrahydrofurfuryl alcohol; N-substituted pyrollidones; dimethyl sulfoxide; 2,2-oxydiethanol; ethylene cyclic carbonate; tetramethyl urewa; thiodiethylene glycol; 1-ethynyl cyclohexanol; tetrahydro-3 furanol, 2,6-dimethyl-m-dioxan-4-ol acetate; and 2,5-bis (hydroxy methyl) tetrahydro furan, other amides, particularly N-alkyl and dialkyl and hydroxy amides, other proton acceptors and buffer systems. Very often high dielectric constant substances will act as mobilizers or initiators.

Electrophoresis of proteins is often done in high pH (alkaline) buffer because of the dependence in electrophoresis on isoelectric points. In contrast, EMP transport of proteins may be carried out in acid media. Buffers may be prepared from the list of biologically compatible agents given above, or may be of the more commonly used Tris, Veronal or Sorensen types. In addition, more common organic acids and bases may be used. Examples of acid buffers useful for EMP transport of proteins and related substances are:

tetra methyl ammonium hydroxide/acetic acid
    triethylene tetramine/2,2-oxydiacetic acid
    dimethyl amine/picric acid
    diethanolamine/dichloracetic acid
    triethanolamine/dichloracetic acid
    piperazine/dichloracetic acid Media prepared as described above, with combination of water, one or more suppressants, one or more agents for increasing the dielectric constant, and one or more initiators (and/or mobilizers) may effect separation of proteins within a minute or so in a few centimeters of Whatram No. 1 filter paper, while the same separation on the same substrate would take up to 16 hours over as much as 15 cm. of substrate with electrophoresis.

A number of proteins and related substances are insoluble in water. For example, some derived or conjugated proteins, as well as some polypeptides, keratins and prolamines, are water insoluble. While this problem may be overcome in some instances, as with zein (prolamine) by use of the modified aqueous media described above, the use of nonaqueous media provides additional flexibility.

An alternative to aqueous EMP systems for proteins and other biochemical compounds is the use of other solvents analogous to water in proton donor number (DN=18.0 for water) and dielectric constant (DC=81.0 for water). Especially useful are ethylene cyclic carbonate (DN=16.4, DC=89.1, boiling point (BP) = 245° C.) and propanediol-1, 2-carbonate (DN=15.1, DC=69.0, BP=240° C.). These solvents contribute superior heat stability to the media formulation, permitting operation with greater resistivity and higher voltage gradients without need for external cooling.

Certain solvents show a more intense solvent action than does water for some proteins. Thus, keratins which are water insoluble may be dissolved in other solvents such as dimethyl sulfoxide. Prolamines may be solubilized in glycols, glycol ethers and certain alcohols.

Solvents of moderate to strong proton acceptor properties are suitable for protein solubilization, and may even form the basis of the media. Solvents of this type include iodine monochloride, sulfer dioxide and hydrogen fluoride. For example, anhydrous hydrogen fluoride is a good solvent for fibrous proteins normally insoluble in water. The collagenous substances, as well as elastins and reticulins are particularly resistant to solubilization in aqueous media, whereas they are soluble in nonaqueous media.

The media for EMP transport of proteins may include other protein solvents chosen to provide particular properties, such as glycols, amides, ethers, pyrrolidones, lactones, sulfoxides, phenols, alcohols and phosphonates.

Suitable aqueous systems for the transport of proteins, in accordance with the foregoing table of suppressants using a solvent/water volume ratio of 16/9 are:
    16 ml. thiodiethylene glycol
    9 ml. water
    2 drops ethanolamine
    (separation of protein mixtures including
    cytochrome C and myoglobin — electrical
    characteristic of 1.8 Kv/1.2 ma)
    16 ml. 6-hexanolactone
    9 ml. water
    3 drops ethanolamine
    (gave protein movement and resolution -
    electrical characteristic of 1 Kv/1.2 ma)
    16 ml. dimethyl acetamide
    9 ml $H_2O$
    4 drops ethanolamine
    (separation of proteins -
    electrical characteristic of 1.6 Kv/1.2 ma)

The following three examples illustrate nonaqueous media representative of those which have been used for EMP transport of human and bovine albumin, hemoglobin, cytochrome C (an enzyme), myoglobin (muscle protein) and pancreatin. In addition, proteins have been separated from whole blood in experiments in which the cell debris remained at the origin. Phenol was a useful media component in these last separations.

EXAMPLE 25

12 ml. — ethylene cyclic carbonate
6 ml. — ethoxyethoxy ethanol
6 ml. — thiodiethylene glycol
6 drops tris-dichloracetic acid buffer

EXAMPLE 26

7 ml. — ethylene cyclic carbonate
7 ml. — ethoxy ethoxy ethanol
9 ml. — oxydiacetic acid
1.5 ml. — formamide
6 drops tris-dichloracetic acid buffer

EXAMPLE 27

10 ml. — ethylene cyclic carbonate
4 ml. — N-methyl pyrrolidone
3 ml. — furfuryl alcohol
2.5 gm. — boric acid
4 ml. — 1,3-butylene glycol
16 drops piperazine-dichloracetic acid buffer (Ph 3.7)
    Acridine orange (fluorescent indicator) .

The following example illustrates EMP media and electrical conditions used for the separation of albumins and especially globulins.

| EXAMPLE | SOLVENT FORMULAE | ELECTRICAL CHARACTERISTICS (Stabilized) |
|---|---|---|
| 28 | 10ml. ethylene cyclic carbonate 4 ml. butylene glycol, 4 ml. methyl pyrrolidonone, 2 ml. | 5.2 KV/2.0–3.6ma Whatman #1 (10 cm.) |

| EXAMPLE | SOLVENT FORMULAE | ELECTRICAL CHARACTERISTICS (Stabilized) |
|---|---|---|
| | -continued formamide (initiator), 2.5 g boric acid, 3 ml. furfural (pH buffer and mobilizer), 16 drops piperazine dichloroacetic acid buffer pH 3.7 (pH buffer and mobilizer), acridine yellow (fluorescent indicator) | |

The same media was used to separate cytochrome C, hemoglobin, myoglobin, albumin, yohimbine, and atropine under the following conditions:

| EXAMPLE | SOLVENT FORMULAE | ELECTRICAL CHARACTERISTICS (Stabilized) |
|---|---|---|
| 29 | 10 ml. ethylene cyclic carbonate, 4 ml. butylene glycol, 4 ml. methyl pyrrolidinone, 2 ml. formamide (initiator), 2.5 g boric acid, 3 ml. furfural (pH buffer and mobilizer), 16 drops piperazine dichloroacetic acid buffer pH 3.7 (pH buffer and mobilizer), acridine yellow (fluorescent indicator) | 4.4 KV/3.6ma; 2.2 KV/1.2ma Whatman #3 |

The use of dyes which act as tracers may be desirable in some cases to visually follow the separation of colorless biochemical species. See examples 27-29 above. It must be established that the particular dye does not interfere with the resolution process itself. Bromphenol blue has been commonly used with serum proteins, but may migrate separately from the protein in EMP. For redox sensitive materials, methylene blue is often suitable, and glutathione either in oxidized or reduced form may be used to buffer against redox reactions. Saframin-type dyes bind to and alter the solubility characteristics of proteolytic enzymes and can therefore be useful in separating them from other materials. A few milligrams of an easily coupled fluorescent tracer such as acridine orange will allow visual observation of many substances including proteins under ultraviolet light without altering their migration characteristics. Other tracers such as brightening agents, fluorescent coupling agents, and even fluorescent antibody material may be useful in following protein transport. Additional tracer agents for biochemical and other work are vital dyes such as the flavines and primulin. Nile blue may be especially useful alone or in combination with other dyes under U.V. and daylight. Neutral red with aesculin remains sensitive at about 1000x dilution with daylight alone. The U.V. dyes are also convenient for localizing weak positive or negative charges in biological structures. Antibodies or other coupling tracer materials as well as radioactive derivatives can also be useful, e.g., rhodamine B-isothiocyanate; fluorescein isothiocyanate; p-isothiocyanato acridine; 4-chloro methyl-1-acridine; 1-ethyl-2-[-3-(1-ethyl naphthol [1,2δ] - thiazolin-2-ylidine)-2-methyl propenyl]-naphth [1,2] thiazolium bromide. Additional possible tracers are phenazine methosulfate, Remazol brilliant blue R, thiazolyte blue, protoporhyrin IX, citrazinic acid, quinine, lisamine, rhodamines, cleves acid and umbelliferone.

Another aspect of the present invention is the use of the technique of EMP media formulation to fabricate gaseous semiconductive media which will allow controlled conduction without need for evacuation, very high temperatures, or very high voltages. The application of the techniques of formulation of liquid EMP media to gaseous media formulation led to the achievement of high levels of conductivity without the need for high potential. The aim in construction of a gaseous EMP media is to increase the conductivity level of the gas to the level of semiconductivity or other level convenient for the desired application.

Industry has made use of gases largely as insulators. Most gaseous conduction performed currently focuses on the high dielectric characteristics of gases generally. The conduction commonly takes place within an envelope or other controlled environment in a relative vacuum with the use of an energy source (such as a thermoelectric filament) to control conduction. In such devices the presence of materials of lesser dielectric character is deleterious. Gaseous conductivity is also of importance currently in the area of ionization or the plasma state. Attempts have been made to produce electricity through the motion of conductive gases relative to a magnetic field (magnetogasdynamics) but it has been found necessary to employ temperatures so high that corrosion of the containers resulted. It is now possible to achieve conductive gases at or near room temperature through the use of EMP, and thereby may be possible to provide a practical means for producing electricity.

Formulation of gaseous EMP media provides a useful scientific technique for investigating the molecular characteristics of materials. In addition, it may be employed in the construction of controlled gaseous conduction devices used for wireless transmission (e.g., in coilless transformer cores), in light emission studies, gaseous charge transport, gaseous molecular transport, electrically mediated gaseous diffusion, and low potential spark gap devices. EMP media formulation may be employed to modify fuel combustion systems and the fuel itself in combustion engines so as to extend the spark propagation distance (e.g., allow separation of the spark plug electrodes by larger distances thus relying less on explosive propagation).

Similar principles to those applied in preparation of liquid semiconductive EMP media are applied in the preparation of gaseous semiconductive EMP media. Media containing a number of components, such as three- and four-way systems, are necessary to effect a substantial alteration in conductivity of the gas to bring it into the semiconductive range. Agents which acting together facilitate proton donor/acceptor interaction, increased conductivity and enhanced dielectric constant are indicated.

For example, water acts by hydrogen bonding in the vapor phase as both a donor and acceptor molecule, interacting with proton donors ranging from strong acids to alkanols (e.g., 1,1,1,3,3,3,-hexafluoropropan-2-ol) and with acceptors such as amines (including pyridines), ethers, alcohols and ketones. In general, the more conductive or active EMP solvents have been found particularly suited to gaseous conduction. (See the list of active agents above.) Also, comixing of materials helps to effect enhanced conductivity.

For example, placing a few drops of triethylene tetramine in the base of a glass test tube seated in a mildly heated sand bath reduced the resistance between the electrodes located 0.5 cm apart and 2.5 cm. from the bottom of the tube to $10^6$ ohms from more than $10^9$ ohms in air. The addition of a small crystal of iodine reduced the resistance to less than $8 \times 10^5$ ohms. Addition of formamide instead of iodine gave $1.5 \times 10^6$ ohms, and two together reduced to less than $5 \times 10^5$ ohms. With some media, resistances in the hundreds of ohms were obtained at low voltages (5–10v) near room temperature and atmospheric pressure.

As a further example, in such a cell, at a five volt potential, a media was formulated from agents (A.) added stepwise by measuring the resistance (B.) obtained after each step in the sequence of addition (C.)

| | | (C.) Sequence of Addition | |
|---|---|---|---|
| (A.) Agent | (B.) Resistance in Cell | Amount Added | Cumulative Amount in Mixture |
| Tetra methyl urea | ∞ (>100 meg ohms) | 5 pts | 5 pts |
| + N-methyl acetamide | 1.70 megΩ | 1.5 pts | 6.5 pts |
| + I$_2$ | 75 k Ω | 1 pts | 7.5 pts |
| + diethylamine | 18 K Ω | 1.5 pts | 9 pts |

Agents which are useful to formulate gaseous EMP Media include iodine, other halogens, amines, volatile salts, amides, nitro derivatives including nitrosylchloride, acid chlorides, hydrazine, oxyhalides, sulfer dioxide, hydrogen fluoride, ammonia, or other potent proton donor or acceptor molecules, combinations thereof, and substances liberating such. Semiconductive media formulated from such components according to the principles of liquid media formulation as modified above provide a controllable conductive gaseous environment even at atmospheric pressure in air. The use of high boiling chemicals as classified for liquid EMP media use requires an elevated temperature to produce the gaseous EMP effect. Use of lower boiling solvents is therefore advantageous in the preparation of gaseous EMP media.

Gaseous EMP media may be subjected to voltages of, for example, 0.5 to 30,000 v/cm, with continuous conduction (rather than sparking) resulting. Modifying agents may be included in the media so as to make it susceptible to arc over in the range of 50 to 30,000 v/cm and therefore useful in fuel systems so as to modify or extend the spark propagation properties and/or electrothermal vaporization prior to ignition.

A further aspect of the present invention is the practice of EMP within a gel. The gel consistency may range from fluid to rigid. Gels generally are susceptible to resistance adjustment by addition of a small amount of conductivity agent with a material of high dielectric constant such as formamide or another amide or akylamide derivative and a coupling solvent if necessary to improve miscibility. The EMP media may be washed into the gel or the gel fabricated with the media in it. One difficulty with the use of gels as EMP media is that by products left over from the gel formation process must be removed if they interfere with the EMP conductivity adjustment and transport.

Agar gel, polyvinyl alcohol (PVA), silica gel, starch gel, Carbopol (carboxypolymethylene) and "Crash Safe Aviation Jet Fuel" (additive-modified kerosene) are examples of gels which function as EMP media when doped with the appropriate conductivity-modifying agents in accordance with the principles described above. Acrylamides could also be employed. An example of a gel fabricated with an EMP solvent within it is PVA gelled with tetrahydrofurfural alcohol. Tetraethyl ortho silicate which gives a clear glass-like gel with numerous organic gels permits compatability with various organic EMP media. Gelatin also provides a clear gel base. Examples of chemical species which may be transported in such gels include dye molecules, and even particulate matter may be moved at fast rates in a "fluid" gel such as crash safe aviation fuel.

Voltage and current levels are adjusted just as in cellulose supported EMP. A slightly higher current, than 1.2 ma/50 cm$^2$ can also be used for thin slabs of gel (to ⅛"). Otherwise, gels ⅜" to ½" thick or greater require careful current consideration to avoid excessive heat buildup.

In EMP separation processes, gels are capable of providing enhanced resolution because of their fine pore structure. EMP induced movement of dye molecules within a gel may be used as an analytical technique to study the structure and properties of the gel itself.

The apparatus used for gel EMP differed from that used for liquid EMP in that the filter paper substrate was replaced with the gel.

EMP within a gel is illustrated by the examples below.

| EX. | SOLVENT FORMULAE |
|---|---|
| 30 | glycol, ammonium bromide (to form a saturated solution in N-methyl pyrolidinone), and formamide. |
| 31 | 5% weight/volume ceresin or microwax in 20% or 30% xylene plus EMP media components appropriate for use with xylene. |

The EMP media components referred to in Example 31 may be the four-way system described at page 12 or ammonium bromide in methoxy ethoxy ethanol, 2(2-ethoxy ethoxy) ethanol, dimethyl formamide, dimethylacetamide, dimethyl sulfoxide, n-butanol, or N-methyl pyrrobidinone.

EMP is susceptible of application to a wide variety of uses, a number of which have been detailed above. The application of EMP to several specialized areas will be further described here.

EMP may be used in conjunction with media phase control to provide an information storage, processing and display mechanism. For example, a media may be used which is solid at ambient temperature, which melts or at least increases in fluidity when warmed. Dye molecules or other detectable or traceable materials in the media may be transported by application of a potential difference when the media is fluid, and stored with display capabilities when the media is rendered non-fluid. The system is non-volatile; the resolidification curtails diffusionary information loss, and the positioning of the dye spots in the solidified media provides for information storage. Gel or porous media might also be used for information storage and display. A permeable solid support substrate may be incorporated in the system to minimize thermal diffusion. By use of a transparent substrate with refractive index approximating that of the liquid media, additional clarity can be achieved. Parallel capillaries, e.g. of glass, may be used to limit diffusion and fix the geometry of the system. Transparent electrodes (e.g., NESA glass) may be used for display purposes.

EMP is particularly suited for this application in a number of respects. The high response speed of EMP systems would allow, for example, response times of less than a second with a 10 cm/min transport rate between parallel plate electrodes 1 mm apart. In addition, different threshold currents may be used to selectively transport a sequence of chemical species for superimposed displays within a single EMP unit or cell.

The components of EMP media which are suitable for use in an information storage and display system are generally those with melting points in the neighborhood of room temperature. From any class of compounds whose use in the media is indicated, one or more media components may be chosen for their melting point. For example, the class of phenols offers the following choices:

| Compound | Melting Point |
| --- | --- |
| 2,4-dichlorophenol | 40–42 |
| 2,4-dimethylphenol | 22–24 |
| 2,6-dimethylphenol | 45–47 |
| 2,4-ditertiary-pentylphenol | 24–26 |
| 2,6-ditertiary-butyl phenol | 35–36 |
| 2,6-ditertiary-butyl-p-cresol | 62–68 |
| o-ethoxyphenol | 25–27 |
| p-methoxyphenol | 54–56 |
| 1-phenyl-2-propanol | 36 |
| thiophenol | 70–75 |

Lower melting compounds, such as 3-phenyl-1-propanol (MP = −18° C.) and m-thiocresol (MP = −20° C.) may be useful in combination with one or more of the compounds listed above.

The use of EMP with melts is not restricted to room temperature melts. Additional media components which may be employed include resins, glasses, glazes and chalcogenides. Glycol-boric acid glasses are low-melting glasses suitable for EMP media. Various mole ratios of boric acid or boric anhydride fused with most glycols yields a rigid transparent glass at room temperature, suitable for modification for EMP use. Starches, sugars, amines, borax and many other compounds can also enter into the glass formation. Increasing the ratio of glycol or amine to the boric acid adjustably lowers the melting point. Similarly, agents such as metallic sterates can act as crystallization retardants and can be used with, for example, sugars to produce glassy EMP media. Rosin and methacrylates are other organic glass forming media. Inorganic glasses can be derived from phosphates, tellurium, selenium and other materials. Iodine, as well as other compatible conductivity agents may be used for adjusting the glass to EMP media requirements.

EMP may be conducted in other solid media by applying heat energy to liquify the media during EMP and allowing the media subsequently to solidify. For example, N-methylacetamide was heated above its melting point and placed on a paper strip (Whatman No.1). The paper strip was suspended between electrodes, rhodamine and ink dyes were then placed on the filter paper and a potential applied across the paper. After the rhodamine dyes migrated, the molten n-methyl-acetamide was allowed to cool and solidify.

Photoconductive materials, such as polyvinyl carbazole, may be employed in conjunction with EMP effectuated information storage, processing and display. For example, in an information reproduction system, a conductive substrate may be coated with polyvinyl carbazole. Where light passing over or through the document, film, object or other image to be reproduced strikes the polyvinyl carbazole, a short circuit will occur, and dye molecules contained in a juxtaposed EMP media will not be caused to move or will be under a reduced potential and therefore subject to reduced movement. Where light does not strike the polyvinyl carbazole, dye molecules may be mobilized or deposited. Because of the fast molecular migration achieved with EMP, such a reproduction process could be carried out at a much lower voltage than used in conventional electrostatic techniques. For example, a process of the type disclosed in U.S. Pat. No. 3,384,566 to Clark could be modified with use of EMP for operation at lower voltage and enhanced transport rates.

EMP may be employed to obtain a number of electro-optic effects. For instance, it may be used in a manner analogous to electrophoresis in fluid glas-sandwich display techniques. See Fluid Glass-Sandwich Display Technique Permits Large, Multicolored Characters, 22 Electronic Engineering Times (March 29, 1974). EMP would provide the advantages of faster response, wider selection of materials and less heat generation compared to electrophoresis in such an application. EMP could also be used in place of electrophoresis in applications such as that described in U.S. Pat. No. 3,511,651 to Rosenberg. EMP Media may additionally be used in electrochromic devices to form the junction material between the electrochromic material of, e.g., molybdenum trioxide on NESA glass and the second electrode. (Sulfuric acid has been employed as the junction fluid in the past.) The technique of EMP media formulation may be used to modify or study liquid crystals.

The technique of EMP media formulation may also be used to modify the Kerr effect (alteration of a material's influence on polarized light by imposition of a high voltage electric field) in various liquids.

Electromagnetic fields in addition to the driving voltage may be employed in connection with EMP for various purposes. A second electrode set at angles to the set providing the driving voltage may be used to cause the chemical species being transported to swerve from a straight line path. Similarly, one or more electrodes angulated to the set providing the driving voltage may be used to compensate for any slight lateral deviation or spreading of a species traveling on a substrate and to counteract the effects of diffusion. In addition, a balanced electrode pair may be placed perpendicular to the path of the chemical species transported, and used to detect the passage of various zones of chemical species based on the change in electrical forces between the second set of electrodes.

Pulsed DC fields may be used instead of a constant DC driving force to reduce media heating. As an additional modification, an AC field may be superimposed on the DC driving force to mediate the dielectric and semiconductive properties of the media, as well as to take advantage of the Debye-Falkenhagen (solvent) effect.

Magnetic fields may be employed to modify the EMP process. A magnetic field, preferably on the order of kilogauss or greater, applied at right angles to the EMP voltage will by virtue of the Faraday magneto-optic effect, cause the D and L forms of stereoisomers transported under the influence of EMP to separate into distinct paths. This procedure must be carried out in an apparatus of special design. A suitable EMP cell comprises two separable electrode compartments and substrate (e.g., filter paper) clamping means. These compartments are mechanically fixed in position so as to allow the pole faces of a powerful electromagnet to be brought within close proximity to the top and underside of the substrate surface. An insulating film such as mylar can be used to retard arc-over to the pole face.

Magnetic fields may be used to stabilize the media so as to reduce long-term diffusion of a molecular species during a continuous EMP process in a manner analogous to that described for electrophoresis in Kolin, Continuous Electrophoretic Fractionation Stabilized by Electromagnetic Rotation, 46 Chemistry 509 (1960). Unlike the Kolin application, there is no significant stabilization problem in EMP due to thermal factors. Further, whereas it has been found that the magnetic response of the migrating species in the aqueous electrophoretic media was nil, the response of species in EMP media as well as the media itself, will differ from electrophoretic aqueous media, and can be further modified and controlled.

The invention herein includes the processes of imparting mobility to or separating chemical species by providing a semiconductive transport medium (which may be liquid, gaseous or solid) and impressing a voltage of about 0.05 to 25,000 volts/cm across the medium sufficiently high to produce a current density in the range of about 0.001 to 400 microamp/cm$^2$ or .002 to 100 microamps/cm$^2$ and equal to or exceeding the threshold current value for the species in the medium, below which value the species remains substantially stationary, to induce a high mobility rate for the species. In an aspect of this invention the fluid semiconductive transport medium contains a component selected from the group consisting of mobilizers and initiators and comprises impressing a voltage within the range of about 0.05 to 50 volts/cm across the medium sufficiently high to produce a current density in the range of about .001 to 4 microamp/cm$^2$, or from about .002 to 0.2 microamps/cm$^2$ and equal to or exceed the threshold current value for the species in the medium, below which value the species remains substantially stationary, to induce a high mobility rate for the species. Where the fluid semiconductive medium comprises water, a conductivity suppressant, a high dielectric constant component, and a component selected from the group consisting of mobilizers and initiators, the process for imparting mobility to a biochemical species is carried out by applying a voltage within the range of about 0.05 to 25,000 volts/cm across the medium sufficiently high to produce a current density of at least 2 micro amps/cm$^2$ or at least 20 microamps and equal to or exceeding the threshold current vallue for the biochemical species in the medium, below which value the biochemical species remains substantially stationary.

Where EMP is carried out on a support member, an adsorbant may be used, such as cellulose, cellulose acetate, cellulose nitrate, alumina, silica, glass, asbestos, wood, flour or resin as Teflon, Pevikon, or ion exchange resin as Amberlite or modified cellulose, or molecular sieve resin as Sephadex, or mineral as diatamaceous earth or apatite.

I claim:

1. A process which comprises imparting mobility to a chemical species by providing a semiconductive transport medium and impressing a voltage of about 0.05 to 25,000 volts/cm across the medium sufficiently high to produce a current density in the range of about 0.001 to 400 microamp/cm$^2$ and equal to or exceeding the threshold current value for the species in the medium, below which value the species remains substantially stationary, to induce a high mobility rate for the species.

2. The process of claim 1 wherein the current density is in the range of about 0.002 to 100 microamp/cm$^2$.

3. A process which comprises imparting mobility to a chemical species by providing a fluid semiconductive transport medium containing a component selected from the group consisting of mobilizers and initiators and impressing a voltage within the range of about 0.05 to 50 volts/cm across the medium sufficiently high to produce a current density in the range of about 0.001 to 4 microamp/cm$^2$ and equal to or exceeding the threshold current value for the species in the medium, below which value the species remains substantially stationary, to induce a high mobility rate for the species.

4. The process of claim 3 wherein the current density is in the range of about 0.002 to 0.2 microamps/cm$^2$.

5. The process of claim 3 wherein the chemical species is on a filter paper support member in the medium.

6. The process of claim 3 wherein the initiators are selected from the group consisting of acetamide, formamide, propionamide, butyramide, hexanamide, lactamide, stearamide, nicatinamide, nepecotamide, benzamide, n-toluamide, salicylamide, iso-valeramide, the methyl, ethyl, propyl, hydroxyethyl, butyl, cyclohexyl or methylal N-substituted and the methyl, ethyl or propyl N, N-disubstituted derivatives of the foregoing compounds, and wherein the mobilizers are selected from the group consisting of guiacol, salicylaldehyde, boric acid, tetrahydrofurfuryl alcohol, tributoxy ethyl phosphate, and 3-acetyl-3-chloropropyl acetate.

7. The process of claim 3 wherein the transport medium exhibits non-linear electrical characteristics upon application of the voltage.

8. The process of claim 3 wherein the chemical species is non-polar.

9. The process of claim 3 wherein a second voltage is impressed across the medium at an angle to the first.

10. A process for separating chemical species which comprises mixing said species with a fluid semiconductive medium containing a component selected from the group consisting of mobilizers and initiators and applying a voltage within the range of about 0.05 to 50 volts/cm across the medium to produce a current density in the range of about 0.001 to 0.2 micro amp/cm$^2$ and equal to or exceeding the threshold current value for at least one species in the medium below which value the species remains substantially stationary.

11. A process which comprises imparting mobility to a biochemical species by
  providing a fluid semiconductive medium comprising water, a conductivity suppressant, a high dielectric constant component, and a component selected from the group consisting of mobilizers and initiators, and
  applying a voltage within the range of about 0.05 to 25,000 volts/cm across the medium sufficiently high to produce a current density of at least 2 micro amps/cm$^2$ and equal to or exceeding the threshold current value for the biochemical species in the medium, below which value the biochemical species remains substantially stationary.

12. The process of claim 11 wherein the conductivity suppressant is selected from the group comprising thiodiethylene glycol; 2,6-dimethyl morpholine; methoxy ethoxy ethanol; 2-pyrollidone; γ-butyrolacetone; sorbitol; 1,3-butanediol; propylene glycol, dimethyl formamide; dimethyl acetamide; tetrahydrofurfuryl alcohol; butoxy ethoxy propanol; 6-hexanolacetone; oxydiethanol; diacetin; ethoxy ethoxy ethoxy ethanol and methoxy methoxy methoxy ethoxy methoxy propanol.

13. The process of claim 11 wherein said voltage is in the range of about 50 to 25,000 volts/cm and said current density at least about 20 microamps/cm$^2$.

14. The process of claim 11 wherein the biochemical species is on a support member in the medium selected from the group consisting of ion-exchange plates, thin-layer plates, cellulose derivative films, agarose gels, acrylamide gels, and silica gels.

15. The process of claim 11 wherein the high dielectric constant component is selected from the group consisting of amides, N-alkyl and N-aryl amides.

16. The process of claim 11 wherein the high dielectric constant component is selected from the group consisting of hydroxy ethyl formamide, N-methyl formamide, formamide, and N-methyl acetamide.

17. The process of claim 11 wherein the component selected from the group consisting of mobilizers and initiators is a proton acceptor.

18. The process of claim 11 wherein the component selected from the group consisting of mobilizers and initiators is selected from the group consisting of N-alkyl, dialkyl, and hydroxy amides.

19. The process of claim 11 comprising a component selected from the group consisting of solvents, mobilizers and initiators selected from the group consisting of nitrobutanol; 3-acetyl 3-chloropropylacetate; salicylaldehyde; N-methylacetamide; boric acid; phenols; guaiacol; fumaric and barbituric acids; piperazine; furfural tributoxy ethylphosphate; β, β, β, -trichloro-t-butyl alcohol; dimethyl-1, 3-dioxolane-4-methanol; 2-ethyl sulfonyl ethanol; tetrahydrofurfuryl alcohol; N-substituted pyrollidones; dimethyl sulfoxide; 2, 2-oxydiethanol; ethylene cyclic carbonate; tetramethyl urea; thiodiethlene glycol; 1-ethynyl cyclohexanol; tetrahydro-3-furanol; 2, 6-dimethyl-m-dioxan-4-ol acetate; and 2, 5-bis (hydroxy methyl) tetrahydro furan.

20. The process of claim 11 wherein the medium further comprises an acid buffer, or alkaline buffer.

21. The process of claim 11 wherein the biochemical species is a protein.

22. A process which comprises imparting mobility to a biochemical species in a nonaqueous medium by providing a fluid semiconductive medium comprising a non-aqueous solvent with proton acceptor properties and applying a voltage within the range of about 0.05 to 25,000 volts/cm across the medium sufficiently high to produce a current density of at least 2 microamps/cm$^2$ and equal to or exceeding the threshold current value for the biochemical species in the medium, below which value the biochemical species remains substantially stationary.

23. The process of claim 22 wherein the nonaqueous solvent is selected from the group consisting of ethylene cyclic carbonate, propanediol-1, 2-carbonate, dimethyl sulfoxide, glycols, glycol ethers, alcohols, iodine monochloride, sulfur dioxide, and hydrogen fluoride.

24. The process of claim 22 wherein the non-aqueous solvent is selected from the group consisting of ethylene cyclic carbonate and propanediol-1, 2-carbonate.

25. The process of claim 24 wherein the semiconductive medium further comprises a phenol.

26. The process of claim 22 wherein said voltage is about 0.005 to 25,000 volts/cm and the current density is at least 20 microamps/cm$^2$.

27. The process of claim 22 wherein the biochemical species is selected from the group consisting of human albumin, bovine albumin, hemoglobin, cytrochrome C, myoglobin, and pancreatin.

28. The process of claim 22 wherein the semiconductive medium further comprises a tracer for the biochemical species.

29. The process of claim 28 wherein the trace is selected from the group consisting of methylene blue and acridine orange.

30. A process for effecting condition in a gas which comprises providing a multi-component gaseous semiconductive medium containing components with proton donor/acceptor interaction capability, high dielectric constant and high conductivity and applying a voltage of about 0.05 to 30,000v/cm to achieve continuous conduction.

31. The process of claim 30 wherein the semiconductive medium comprises components selected from the group consisting of strong acids, alkylols, amines, ethers, alcohols, ketones, halogens, volatile salts, amides, nitro derivatives, hydrazides, acid chlorides, alcohol amines, and oxyhalides.

32. The process of claim 30 wherein the semiconductive medium comprises components selected from the group consisting of triethylene tetramine, formamide, iodine, nitrosylchloride, hydrazine, sulfur dioxide, hydrogen, fluoride, diethylamine, tetramethylurea, N-methylacetamide, and ammonia.

33. A process which comprises imparting mobility to a chemical species by providing a semiconductive transport medium within a gel and impressing a voltage of 0.05 to 25,000 volts/cm across the medium sufficiently high to produce a current density in the range of about 0.001 to 400 micro amp/cm$^2$ and equal to or exceeding the threshold current value for the species in the medium, below which value the species remains substantially stationary, to induce a high mobility rate for the species.

34. The process of claim 33 wherein the semiconductive transport medium within the gel comrises a conductivity agent and a comonent of high dielectric constant.

35. The process of claim 37 wherein said current density is from 0.002 to 100 microamps/cm$^2$.

* * * * *